US012791556B2

(12) United States Patent
De Groot et al.

(10) Patent No.: US 12,791,556 B2
(45) Date of Patent: Nov. 10, 2026

(54) METHOD AND SYSTEM FOR COLLECTING ONE OR MORE CELLULAR BODIES

(71) Applicant: LUMICKS CA HOLDING B.V., Amsterdam (NL)

(72) Inventors: Mattijs De Groot, Amsterdam (NL); Andrea Candelli, Amsterdam (NL); Gerrit Sitters, Amsterdam (NL); Olivier Theodoor Heyning, Amsterdam (NL)

(73) Assignee: LUMICKS CA HOLDING B.V., Amsterdam (NL)

(*) Notice: Subject to any disclaimer, the term of this patent is extended or adjusted under 35 U.S.C. 154(b) by 741 days.

(21) Appl. No.: 18/023,273

(22) PCT Filed: Aug. 26, 2021

(86) PCT No.: PCT/EP2021/073676

§ 371 (c)(1),
(2) Date: Feb. 24, 2023

(87) PCT Pub. No.: WO2022/043467

PCT Pub. Date: Mar. 3, 2022

(65) Prior Publication Data

US 2023/0349895 A1 Nov. 2, 2023

(30) Foreign Application Priority Data

Aug. 27, 2020 (NL) ...................................... 2026358

(51) Int. Cl.
*G01N 33/543* (2006.01)
*B01L 3/00* (2006.01)

(52) U.S. Cl.
CPC .. *G01N 33/54386* (2013.01); *B01L 3/502761* (2013.01); *B01L 2200/0652* (2013.01); *B01L 2300/0654* (2013.01)

(58) Field of Classification Search
CPC ..... B01L 2200/0652; B01L 2300/0654; B01L 3/502761; G01N 15/00; G01N 15/01;
(Continued)

(56) References Cited

U.S. PATENT DOCUMENTS

| | | | |
|---|---|---|---|
| 7,049,579 | B2 | 5/2006 | Ozkan et al. |
| 7,081,192 | B1 | 7/2006 | Wang et al. |

(Continued)

FOREIGN PATENT DOCUMENTS

| | | | |
|---|---|---|---|
| CN | 110343603 | A | 10/2019 |
| CN | 111157616 | A | 5/2020 |

(Continued)

OTHER PUBLICATIONS

Archbold, E. and Ennos, A.E. "Observation of Surface Vibration Modes by Stroboscopic Hologram Interferometry", Nature, Mar. 9, 1968, pp. 942-943, vol. 217.

(Continued)

*Primary Examiner* — Jennifer Wecker
(74) *Attorney, Agent, or Firm* — Steven M. Koehler; Westman, Champlin & Koehler, P.A.

(57) ABSTRACT

A method for collecting one or more cellular bodies in dependence on their binding force with a sample surface is disclosed. The method comprises providing a sample holder comprising a holding space. The holding space comprises, e.g. is substantially filled with, a fluid medium and comprises the sample surface and the one or more cellular bodies in the fluid medium. Further, the one or more cellular bodies are contacting said sample surface. The method also comprises rotating the sample holder around an axis of rotation for causing a centrifugal force on the one or more cellular bodies herewith separating the one or more cellular bodies from the sample surface. The method also comprises collecting the separated one or more cellular bodies. Also, a (Continued)

method for detection cellular bodies is described. This disclosure further relates to corresponding systems, computer-implemented methods, computer programs and computer-readable storage media having stored such computer programs.

13 Claims, 15 Drawing Sheets

(58) Field of Classification Search
CPC ........... G01N 33/5005; G01N 33/5076; G01N 33/5079; G01N 33/5082; G01N 33/54366; G01N 33/54386
See application file for complete search history.

(56) References Cited

U.S. PATENT DOCUMENTS

| | | | |
|---|---|---|---|
| 7,612,355 | B2 | 11/2009 | Wu et al. |
| 8,795,143 | B2 | 8/2014 | Wong et al. |
| 9,298,968 | B1 | 3/2016 | Peljto et al. |
| 9,453,787 | B2 | 9/2016 | Foster et al. |
| 2002/0076825 | A1 | 6/2002 | Cheng et al. |
| 2002/0162393 | A1 | 11/2002 | Kaduchak et al. |
| 2003/0015035 | A1 | 1/2003 | Kaduchak et al. |
| 2003/0194697 | A1 | 10/2003 | Klenerman et al. |
| 2004/0150296 | A1 | 8/2004 | Park et al. |
| 2006/0021437 | A1 | 2/2006 | Kaduchak et al. |
| 2006/0024206 | A1 | 2/2006 | Sinha et al. |
| 2007/0184433 | A1 | 8/2007 | Tao et al. |
| 2007/0220970 | A1 | 9/2007 | Gruber |
| 2009/0139332 | A1 | 6/2009 | Goddard et al. |
| 2010/0000325 | A1 | 1/2010 | Kaduchak et al. |
| 2011/0127164 | A1 | 6/2011 | Sinha et al. |
| 2011/0207238 | A1 | 8/2011 | Horri et al. |
| 2012/0298236 | A1 | 11/2012 | Goddard et al. |
| 2013/0014826 | A1 | 1/2013 | Kaduchak et al. |
| 2013/0218048 | A1 | 8/2013 | Hayden et al. |
| 2013/0225429 | A1 | 8/2013 | Curry |
| 2014/0033808 | A1 | 2/2014 | Ding et al. |
| 2014/0226430 | A1 | 8/2014 | Bloch |
| 2015/0017678 | A1 | 1/2015 | Matula et al. |
| 2015/0258470 | A1 | 9/2015 | Kaduchak et al. |
| 2016/0243560 | A1 | 8/2016 | Wong et al. |
| 2017/0056849 | A1 | 3/2017 | Bloch |
| 2017/0121658 | A1 | 5/2017 | Hinojosa et al. |
| 2017/0121659 | A1 | 5/2017 | Hinojosa et al. |
| 2017/0121663 | A1 | 5/2017 | Hinojosa et al. |
| 2017/0122912 | A1 | 5/2017 | Fattinger et al. |
| 2017/0139192 | A9 | 5/2017 | Halvorsen et al. |
| 2017/0216793 | A1 | 8/2017 | Bloch |
| 2017/0299492 | A1 | 10/2017 | Rindorf et al. |
| 2017/0328834 | A1 | 11/2017 | Matula et al. |
| 2018/0080049 | A1* | 3/2018 | Waters .................. A61K 40/11 |
| 2018/0217146 | A1 | 8/2018 | Varadarajan et al. |
| 2018/0257076 | A1 | 9/2018 | Weitz et al. |
| 2019/0255527 | A1 | 8/2019 | Candelli et al. |
| 2020/0129936 | A1 | 4/2020 | Bloch |
| 2020/0129937 | A1 | 4/2020 | Bloch |
| 2020/0129938 | A1 | 4/2020 | Bloch |
| 2020/0129939 | A1 | 4/2020 | Bloch |
| 2021/0018503 | A1 | 1/2021 | Varadarajan et al. |
| 2021/0041446 | A1 | 2/2021 | Takahashi et al. |
| 2021/0247291 | A1 | 8/2021 | Wuite et al. |
| 2022/0203359 | A1 | 6/2022 | Chiou et al. |
| 2022/0366708 | A1 | 11/2022 | Van Der Horst |

FOREIGN PATENT DOCUMENTS

| | | | |
|---|---|---|---|
| EP | 3418745 | A1 | 12/2018 |
| NL | 2024155 | B1 | 7/2021 |
| WO | 2004054704 | A1 | 7/2004 |
| WO | 2005001440 | A1 | 1/2005 |
| WO | 2005107939 | A1 | 11/2005 |
| WO | 2014200341 | A1 | 12/2014 |
| WO | 2016154620 | A1 | 9/2016 |
| WO | 2017147398 | A1 | 8/2017 |
| WO | 2018083193 | A2 | 5/2018 |
| WO | 2019212349 | A2 | 11/2019 |
| WO | 2020153837 | A1 | 7/2020 |
| WO | 2020219831 | A1 | 10/2020 |
| WO | 2021089654 | A1 | 5/2021 |
| WO | 2022045892 | A1 | 3/2022 |
| WO | 2022050839 | A1 | 3/2022 |
| WO | 2022066009 | A1 | 3/2022 |
| WO | 2022066011 | A1 | 3/2022 |
| WO | 2022075844 | A1 | 4/2022 |
| WO | 2022075848 | A1 | 4/2022 |
| WO | 2023274951 | A1 | 1/2023 |
| WO | 2023275257 | A1 | 1/2023 |
| WO | 2023277691 | A1 | 1/2023 |
| WO | 2023085925 | A1 | 5/2023 |

OTHER PUBLICATIONS

Barnkob et al. "Measuring the Local Pressure Amplitude in Microchannel Acoustophoresis", Lab on a Chip, 2010, pp. 563-570, vol. 10.
Barnkob et al. "General Defocusing Particle Tracking", Lab on a Chip, 2015, pp. 3556-3560, vol. 15.
Baudoin et al. "Spatially Selective Manipulation of Cells with Single-Beam Acoustical Tweezers", Nature Communications, 2020, pp. 1-10, vol. 11, No. 1.
Bruus, H. "Acoustofluidics 7: the Acoustic Radiation Force on Small Particles", Lab on a Chip, 2012, pp. 1014-1021, vol. 12.
Cacace et al. "Digital Holography as 3D Tracking Tool for Assessing Acoustophoretic Particle Manipulation", Optics Express, Jul. 24, 2017, 7 pp. 17746-17752, vol. 25, No. 15.
Carlson et al. "Tracking Simple Cells in Live Animals Using a Photoconvertible Near-Infrared Cell Membrane Label", PLOS One, Aug. 2013, 10 pages, vol. 8, No. 8.
Cheezum et al. "Quantitative Comparison of Algorithms for Tracking Single Fluorescent Particles", Biophysical Journal, Oct. 2001, pp. 2378-2388, vol. 81, No. 4.
Choi et al. "Microfluidic Deformability-activated Sorting of Single Particles", Microsystems & Nanoengineering, 2020, 9 pages, vol. 6, No. 11.
Cuche et al. "Digital Holography for Quantitative Phase-Contrast Imaging", Optics Letters, Mar. 1, 1999, vol. 24, No. 5.
Cuche et al. "Simultaneous Amplitude-Contrast and Quantitative Phase-Contrast Microscopy by Numerical Reconstruction of Fresnel Off-Axis Holograms", Applied Optics, Dec. 1, 1999, vol. 38, No. 34.
Dual et al. "Acoustofluidics 6: Experimental Characterization of Ultrasonic Particle Manipulation Devices", Lab on a Chip, Jan. 1, 2012, vol. 12, No. 5.
Evander, M. and Nilsson, J. "Acoustofluidics 20: Applications in Acoustic Trapping", Lab on a Chip, 2012, pp. 4667-4676, vol. 12.
Evander et al. "Noninvasive Acoustic Cell Trapping in a Microfluidic Perfusion System for Online Bioassays", Analytical Chemistry, Apr. 1, 2007, pp. 2984-2991, vol. 79, No. 7.
Gosse, C. and Croquette, V. "Magnetic Tweezers: Micromanipulation and Force Measurement at the Molecular Level", Biophysical Journal, Jun. 2002, pp. 3314-3329, vol. 82, No. 6.
Grimm et al. "Bright Photoactivatable Fluorophores for Single-Molecule Imaging", BioRxiv, Apr. 4, 2016, 19 pages, retrieved from https://www.biorxiv.org/content/10.1101/066779v2.full.pdf.
Halabi et al. "Dual-Activatable Cell Tracker for Controlled and Prolonged Single-Cell Labeling", ACS Chemical Biology, Apr. 16, 2020, pp. 1613-1620, vol. 15.
Hammarström et al. "Frequency Tracking in Acoustic Trapping for Improved Performance Stability and System Surveillance", Lab on a Chip, 2014, pp. 1005-1013, vol. 14.
Hariharan, P. and Oreb, B.F. "Stroboscopic Holographic Interferometry: Application of Digital Techniques", Optics Communications, Aug. 15, 1986, pp. 83-86, vol. 59, No. 2.
Helderman et al. "Three-dimensional Intracellular Optical Coherence Phase Imaging", Optics Letters, Feb. 15, 2013, pp. 431-433, vol. 38, No. 4.

(56) References Cited

OTHER PUBLICATIONS

Jaqaman et al. "Robust Single-particle Tracking in Live-cell Time-lapse Sequences", Nature Methods, Aug. 2008, pp. 695-702, vol. 5, No. 8.
Joo et al. "Spectral-Domain Optical Coherence Phase Microscopy for Quantitative Phase-Contrast Imaging", Optics Letters, 2005, pp. 2131-2133, vol. 30, No. 16.
Kamsma, D and Wuite, G. "Acoustic Force Spectroscopy (AFS)—From Single Molecules to Single Cells", PHD-thesis Vrije Universiteit Amsterdam, 2018, 183 pages.
Kamsma et al. "Tuning the Music: Acoustic Force Spectroscopy (AFS) 2.0", Methods, 2016, pp. 26-33, vol. 105.
Kamsma et al. "Single-cell Acoustic Force Spectroscopy: Resolving Kinetics and Strength of T Cell Adhesion to Fibronectin", Cell Reports, Sep. 11, 2018, pp. 3008-3016, vol. 24.
Kuznetsova et al. "Applications of Ultrasound Streaming and Radiation Force in Biosensors", Biosensors and Bioelectronics, Feb. 2, 2007, pp. 1567-1577, vol. 22, No. 8.
Marx, V., "Biophysics: Using Sound to Move Cells", Nature Methods, 2015, pp. 41-44, vol. 12, No. 1.
Merritt et al. "High Multiplex, Digital Spatial Profiling of Proteins and RNA in Fixed Tissue Using Genomic Detection Methods", Nature Biotechnology, May 11, 2020, pp. 586-599, vol. 38.
Muller et al. "Ultrasound-induced Acoustophoretic Motion of Microparticles in Three Dimensions", Phyiscal Review E, Aug. 2013, 13 pages.
Mulvana et al. "Ultrasound Assisted Particle and Cell Manipulation on-chip", Advanced Drug Delivery Reviews, 2013, pp. 1600-1610, vol. 65, No. 11-12.
Nguyen et al. "Microchip Based Microrheology via Acoustic Force Spectroscopy Shows That Endothelial Cell Mechanics Follows a Fractional Viscoelastic Model", bioRxiv, Jul. 3, 2020, 45 pages.
Oiwa et al. "Steady-state Force-velocity Relation in the ATP-dependent Sliding Movement of Myosin-coated Beads on Actin Cables in vitro Studied with a Centrifuge Microscope", Proceedings of the National Academy of Sciences, Oct. 1, 1990, pp. 7893-7897, vol. 87, No. 20.
Osseiran et al. "Longitudinal Monitoring of Cancer Cell Subpopulations in Monolayers, 3D Spheroids, and Xenografts Using the Photoconvertible Dye DiR", Scientific Reports, Apr. 5, 2019, 10 pages, vol. 9, No. 5713.
Pereiro et al. "Nip the Bubble in the Bud: a Guide to Avoid Gas Nucleation in Microfluidics", Lab on a Chip, Jun. 6, 2019, pp. 2296-2314, vol. 19.
Qin et al. "Organic Fluorescent Thermometers: Highlights from 2013-2017", TrAC—Trends in Analytical Chemistry, May 2018, pp. 259-271, vol. 102.
Sarkar et al. "Multiplexed Affinity-Based Separation of Proteins and Cells Using Inertial Microfluidics", Scientific Reports, Mar. 30, 2016, pp. vol. 6, No. 1.
Shajenko, P. and Johnson, C.D., "Stroboscopic Holographic Interferometry", Applied Physics Letters, Jul. 1, 1968, pp. 44-46, vol. 13, No. 1.
Sorkin et al. "Probing Cellular Mechanics with Acoustic Force Spectroscopy", Molecular Biology of the Cell, Aug. 8, 2018, pp. 2005-2011, vol. 29.
Telschow et al. "Full-Field Imaging of Gigahertz Film Bulk Acoustic Resonator Motion", IEEE Transactions on Ultrasonics, Ferroelectrics, and Frequency Control, Oct. 2003, pp. 1279-1285, vol. 50, No. 10.
Thalhammer et al. "Acoustic Force Mapping in a Hybrid Acoustic-Optical Micromanipulation Device Supporting High Resolution Optical Imaging", Lab Chip, 2016, pp. 1523-1532, vol. 16.
Turcotte et al. "Intravital Multiphoton Photoconversion with a Cell Membrane Dye", Journal of Biophotonics, Feb. 2017, pp. 206-210, vol. 10, No. 2.
Van Loenhout et al. "Non-bias-limited Tracking of Spherical Particles, Enabling Nanometer Resolution at Low Magnification", Biophysical Journal, May 2012, pp. 2362-2371, vol. 102.
Wang et al. "A Silicon-based Ultrasonic Immunoassay for Detection of Breast Cancer Antigens", Sensors and Actuators, Jun. 25, 1998, pp. 13-21, vol. 49, No. 1-2.
Wang et al. "Image Quality Assessment: From Error Visibility to Structural Similarity", IEEE Transactions on Image Processing, Apr. 1, 2004, vol. 13, No. 4.
Wang et al. "Single-cell Compressibility Quantification for Assessing Metastatic Potential of Cancer Cells Through Multi-frequency Acoustophoresis", Microfluidics and Nanofluidics, 2018, 7 pages, vol. 22, No. 68.
Watrasiewicz, B. M. and Spicer, P. "Vibration Analysis by Stroboscopic Holography", Nature, Mar. 23, 1968, pp. 1142-1143, vol. 217.
Zhang, H. and Liu, K. "Optical Tweezers for Single Cells", Journal of the Royal Society Interface, Apr. 1, 2008, pp. 671-690, vol. 5, No. 24.
Garcia et al. "Quantification of Cell Adhesion Using a Spinning Disc Device and Application to Surface-Reactive Materials", Biomaterials, Dec. 31, 1997, pp. 1091-1098, vol. 18, No. 16.
Halvorsen, K. and Wong, W., "Massively Parallel Single-Molecule Manipulation Using Centrifugal Force", Biophysical Journal, Dec. 29, 2009, 4 pages.
Lotz et al. "Cell Adhesion to Fibronectin and Tenascin: Quantitative Measurements of Initial Binding and Subsequent Strengthening Response", The Journal of Cell Biology, Oct. 1, 1989, pp. 1795-1805, vol. 109, No. 4.
Nguyen et al. "A Centrifuge Method to Measure Particle Cohesion Forces to Substrate Surfaces: the Use of a Force Distribution Concept for Data Interpretation", International Journal of Pharmaceutics, Jun. 30, 2010, pp. 88-95, vol. 393, No. 1-2.
International Search Report and Written Opinion of corresponding International Patent Application No. PCT/EP2021/073676 dated Dec. 7, 2021.

* cited by examiner

| time | $\omega$ | distance, r (m) | collecting surface |
|---|---|---|---|
| $t_1$ | $\omega_1$ | 0,3 | $24_1$ |
| $t_2$ | $\omega_2$ | 0,3 | $24_2$ |
| $t_3$ | $\omega_3$ | 0,3 | $24_3$ |
| $t_4$ | $\omega_4$ | 0,3 | $24_4$ |
| $t_5$ | $\omega_5$ | 0,3 | $24_5$ |
| $t_6$ | $\omega_6$ | 0,3 | $24_6$ |

METHOD AND SYSTEM FOR COLLECTING ONE OR MORE CELLULAR BODIES

CROSS-REFERENCE TO RELATED APPLICATION(S)

This Application is a Section 371 National Stage Application of International Application No. PCT/EP2021/073676, filed Aug. 26, 2021, and published as WO 2022/043467 A1 on Mar. 3, 2022, and further claims priority to Netherlands Patent Application No. 2026358, filed Aug. 27, 2020.

FIELD OF THE INVENTION

This disclosure relates to methods and systems for detecting and/or collecting one or more cellular bodies in dependence on their binding force with a sample surface. In particular to such methods and systems wherein cellular bodies are separated from the sample surface using a centrifugal force.

BACKGROUND

The study of cell interactions, e.g. the binding strength of cells on cells is a highly relevant and active research area in biosciences. For example, the avidity characterizes the cumulative effect of multiple individual binding interactions between cells. Similarly, the affinity characterizes the strength with which a cell, e.g. an antibody, binds to a protein complex that is part of a cell membrane of a target cell. The avidity and affinity are examples of parameters that play an essential role in the study and development of therapies in medicine, e.g. immune oncology.

US2016/0243560 discloses an apparatus for measuring a characteristic of a sample. The apparatus includes a sample measurement apparatus, which includes a light source configured to illuminate the sample, and a detector configured to receive light from the sample. The sample measurement apparatus is sized and dimensioned to fit within a centrifuge receptacle, the centrifuge receptacle coupled to a spindle configured to rotate the centrifuge receptacle to apply a force to the sample.

Unfortunately, such apparatus is quite complex to implement and the accuracy it provides in terms of analysing the binding strength of cells is limited. Implementing such apparatus involves installing the light-receiving detector and typically a microscope objective onto a rotatable arm, which poses challenges for the optical alignment of the detector and microscope objective as well as for the instalment of electric cabling that needs to be provided for communication with the light source and detector, for example. Further, the accuracy provided by the apparatus disclosed in US2016/0243560 is limited, because it involves the optical investigation of detachments of particles from a sample surface. This is especially true when the particles are unlabelled. Typically, such sample surface is inhomogeneous and is itself emitting an optical signal which renders it difficult to observe the particles on the sample surface, let alone the detachments of such particles from the surface. Further, with the apparatus as disclosed in US2016/0243560 only a certain focal plane and certain field of view can be investigated meaning that phenomena on the sample that occur outside of the focal plane and/or outside of this field of view are not detected. In any case, since the limited field of view of the detector thus limits the size of the area that can be investigated, only relatively small samples can be studied during each experiment. Therefore, the apparatus of US2016/0243560 is associated with a limited throughput in terms of the sample area that can be studied per unit of time.

In light of the above, there is a need in the art for methods and systems that enable to accurately analyse binding force characteristics of cellular bodies in an easy manner.

SUMMARY

Therefore, a method for collecting one or more cellular bodies in dependence on their binding force with a sample surface is disclosed. The method comprises providing a sample holder comprising a holding space. The holding space comprises, e.g. is substantially filled with, a fluid medium and comprises the sample surface and the one or more cellular bodies in the fluid medium. Further, the one or more cellular bodies are contacting said sample surface. The method also comprises rotating the sample holder around an axis of rotation for causing a centrifugal force on the one or more cellular bodies herewith separating the one or more cellular bodies from the sample surface. The method also comprises collecting the separated one or more cellular bodies.

One aspect of this disclosure relates to a system for collecting one or more cellular bodies in dependence on their binding force with a sample surface. The system comprises a sample holder comprising a holding space for holding the sample surface, a fluid medium and the one or more cellular bodies in contact with the sample surface. The system also comprises a rotation provisioning system configured to rotate the sample holder around an axis of rotation for causing a centrifugal force on the one or more cellular bodies for separating the one or more cellular bodies from the sample surface. Further, the system comprises a collection system for collecting the separated cellular bodies.

Advantageously, this method and system enable accurate analysis of the binding force of cellular bodies to a sample surface. Importantly, the method and system do not require any optical investigation of the sample surface. The inventors have realized that detachments of the cellular bodies from the sample surface, which relate to the binding force of the cellular bodies with the sample surface, can be accurately studied by simply collecting the separated cellular bodies. After they have been collected, they can be further analyzed, for example by removing the collected cellular bodies from the sample holder and counting them.

The collected cellular bodies can originate from anywhere on the sample surface. In principle, all cellular bodies that are initially on the sample surface are tested in the sense that all cellular bodies that do separate due to the applied centrifugal force, can be collected. This, in contrast with for example optical investigation of the sample surface, wherein no information can be obtained about cellular bodies that sit outside of the field of view of the detector. Thus, in the above method and system, the sample surface can be chosen relatively large which enables to analyze the binding force of many cellular bodies during a single experiment. This also enables improved statistical analysis of the binding characteristics simply because more measurements can be obtained per unit of time.

Since the method and system do not necessarily involve optical investigation of the sample, the fluid medium does not have to have a minimum degree of transparency or optical clarity.

Further, this method and system involve the application of a centrifugal force on cellular bodies that are in contact with the sample surface. Such centrifugal force is easily applied, namely by simply rotating the sample holder containing the sample surface and cellular bodies around an axis of rotation. Also, such centrifugal force is highly homogeneous in the sense that each cellular body on the sample surface experiences the same acceleration. This for example in contrast with acoustic force spectroscopy (AFS), which is another technique for studying interactions between cells. For example, WO 2018/083193 describes a so-called acoustic force spectroscopy (AFS) system that is configured to examine interactions between cells by applying a force to the cells. The system includes a microfluidic cell comprising a functionalised wall surface which may include target cells. A plurality of unlabelled effector cells, e.g. T-cells, can be flushed into the microfluidic cell, so that they can settle and bind to target cells. Thereafter, an acoustic source is used to exert a ramping force on the bound effector cells so that effector cells will detach from the target cells at a certain force. During this process, the spatiotemporal behaviour of the effector cells in the microfluidic cells is imaged using an imaging microscope. The interaction between cells, e.g. the force at which the effector cells detach, may be determined by analysing the captured (video) images. For example, the cell avidity of the effector cells can be determined this way. Unfortunately, it is difficult to apply a homogeneous force on the cells across the functionalised wall surface, because of the presence of lateral nodes in the sample holder intrinsic to the acoustic resonator design. Also, manufacturing tolerances lead to further asymmetries and inhomogeneities in typical acoustic force spectroscopy chips, which are also a source of force inhomogeneities across the sample surface.

The systems and methods disclosed herein are further advantageous in that they allow for separating and sorting cellular bodies without requiring microfluidics for flushing separated cellular bodies away, e.g. from the holding space, for downstream collection. Separated cellular bodies, once separated, automatically flow away from the sample surface due to the applied centrifugal force that caused the separation from the sample surface in the first place. Further, it should be appreciated that such microfluidics systems would be very complex to implement in a rotating system for various reasons. The centrifugal force would likely cause unintended fluid flow due to g-stress on tubes, or any other flexible part, as well as on bubbles, et cetera. As a result, the cellular bodies in the sample holder, especially those who are still in contact with the sample surface, would experience unintended shear flows and stresses, which would distort analysis of binding force characteristics. Also, starting fluid flows when the sample holder is already rotating is problematic, because this would require operation of valves, pumps and/or pressure systems in the rotating system or centrifuge. Space constraints and varying g-forces will require complex engineering. Apart from this, such microfluidic systems are expensive and should be regularly cleaned.

The cellular bodies may be cell portions like subcellular organelles, cell nuclei, and/or mitochondria. The cellular bodies may be unicellular or pluricellular, such as small clumped cell groups, plant or animal biopts, dividing cells, budding yeast cells, colonial protists, etc. The cellular bodies may also be animal embryos in an early stage of development (e.g. the morula-stadium of a mammal, possibly a human embryo). In particular cases different types of cellular bodies may be studied together. E.g., cellular bodies from a mucosal swab, blood sample, or other probing techniques could be used. A cellular body may also be one or more immune cells, one or more tumor cells, one or more cells that have been infected, for example by a virus.

As used herein, a centrifugal force on an object may be understood to be an inertial force, also referred to as a fictitious force or pseudo force, that appears to act on the object when viewed in a rotating frame of reference. If the axis of rotation of the frame of reference is selected such that it coincides with an axis of rotation of the object, the centrifugal force is directed radially outwards from this axis.

A binding force of on more cellular bodies as used herein may refer to an avidity of the one or more cellular bodies or an affinity of a receptor or ligand on a cellular body with a ligand or receptor, respectively, on the sample surface. Further, as used herein, one or more cellular bodies contacting a sample surface may refer to the one or more cellular bodies being bound to the sample surface. The sample surface may be a functionalized wall surface that is configured to bind the one or more cellular bodies.

The separated one or more cellular bodies are preferably collected within the sample holder, e.g. within the holding space. As used herein, collecting a set of one or more cellular bodies may be understood to refer to physically grouping together the set of one or more cellular bodies in a certain volume or area, such as in a reservoir or in a certain area of a collecting surface as described below. Preferably, such volume or area then would not contain other cellular bodies that are not within the set of one or more cellular bodies so that the set can be further analyzed separately from such other cellular bodies.

The collection system is for example embodied as a reservoir in which separated one or more cellular bodies end up for example due to the persistent centrifugal force. The collection system is for example embodied as a collecting surface, preferably opposite the sample surface, that is configured to bind separated cellular bodies. Such collecting surface may be a functionalized wall surface.

The fluid medium may be a liquid or a gas, for example. Further, the holding space may be fluid tight, e.g. such that the fluid medium cannot leave the holding space while the sample holder is rotated around the axis of rotation. Additionally or alternatively, the holding space may be closed, e.g. completely closed, and/or at least completely closable, e.g. by a lid and/or cap.

The sample surface is preferably perpendicular to the direction of centrifugal force, e.g. is preferably perpendicular to a radial direction of the rotation axis.

In an embodiment of the method, said one or more cellular bodies comprise a first set of one or more cellular bodies and a second set of one or more cellular bodies. In such embodiment, the method comprises rotating the sample holder at a first angular velocity, $\omega\mathbf{1}$, the sample surface being positioned a distance, $r_1$, from the axis of rotation, $\omega_1^2r_1$ having a first value, for causing a centrifugal force on the one or more cellular bodies herewith separating the first set of one or more cellular bodies from the sample surface. This embodiment also comprises rotating the sample holder at a second angular velocity, $\omega_2$, the sample surface being positioned a distance, $r_2$, from the axis of rotation, $\omega_2^2r_2$ having a second value different from, preferably higher than, said first value, for causing a centrifugal force on one or more cellular bodies still contacting the sample surface herewith separating the second set of one or more cellular bodies from the sample surface. This embodiment also comprises collecting the separated second set of one or more cellular bodies in the fluid medium after they have been separated from the sample surface.

Optionally, this embodiment comprises collecting the separated first set of one or more cellular bodies in the fluid medium after they have been separated from the sample surface. Then, preferably the second set of one or more cellular bodies is collected separately from the first set of one or more cellular bodies. Separately collecting the first and second set of one or more cellular bodies may simply be performed by removing the collected first set of one or more cellular bodies from the holding space, preferably when the sample holder has temporarily stopped rotating around the axis of rotation, and then rotating the sample holder at the second angular velocity to separate the second one or more cellular bodies from the sample surface and thereafter removing the second set of one or more cellular bodies from the sample surface. In an embodiment, the rotation provisioning system of the system is configured to rotate the sample around the axis of rotation at different angular velocities, and/or at different distances between the sample surface and the axis of rotation. The latter may be embodied in that the sample holder is translatable over a rotatable arm of the rotation provisioning system.

These embodiments of the method and system advantageously enable to collect one or more cellular bodies in dependence on their binding force to the sample surface. In particular these embodiments allow to sort cellular bodies in dependence on their binding force to the sample surface. For example, it is possible to first rotate at $\omega i^2 r_1$ for some time period. This causes respective centrifugal forces on respective cellular bodies in dependence on their respective masses m in accordance with $F=m\omega_1^2 r_1$. The rotation also causes a centrifugal force on the fluid medium. If the density of the fluid medium differs from the density of the cellular bodies, then the cellular bodies experience a resulting force. Preferably, this resulting force is directed away from the sample surface. Due to the resulting force, some of the cellular bodies that are contacting, e.g. bound to, the sample surface, separate from the sample surface, for example due to said resulting force on such cellular body being higher than the binding force for this cellular body to the sample surface. These separating cellular bodies may be referred to as the first set of one or more bodies. It should be appreciated that this first set of one or more cellular bodies may be collected, but this is not required. In an example, this first set of one or more cellular bodies is discarded in some manner. This can be performed by stopping the rotation of the sample holder, dismounting the sample holder and flushing the sample holder in some manner. Then, the sample holder, which would then still comprise the sample surface in contact with the second set of one or more cellular bodies can be remounted on the system.

Subsequently, the sample holder may be rotated at $\omega_2^2 r_2$ for some time period, wherein $\omega_2^2 r_2$ has a higher value than $\omega_1^2 r_1$. Then, the second set of one or more cellular bodies will separate from the sample surface and can be collected. Thus, this embodiment allows to single out from all cellular bodies that initially contact the sample surface, a set of one or more cellular bodies that separate from the sample surface when they are accelerated at a certain value, or at a certain value range of course.

It should be appreciated that $r_1$ and $r_2$ may be equal. Alternatively. $\omega_1$ and $\omega_2$ may be equal. In an embodiment, $r_1$ and $r_2$ are different and $\omega_1$ and $\omega_2$ are different. Preferably $\omega_2^2 r_2$ is higher than $\omega_2^2 r_1$.

In principle, any number of sets of one or more cellular bodies can be collected in such manner based on their binding force, such as two sets, which would be the case if said first set of one or more cellular bodies is also collected, three sets, four sets, five sets, or more sets of one or more cellular bodies.

In an embodiment, the method comprises rotating the sample holder at some angular velocity, ω, the sample surface being positioned a distance, r, from the axis of rotation, for causing a centrifugal force on the one or more cellular bodies for some time period. During a first part of this time period, a set of one or more cellular bodies separate from the sample surface due to the centrifugal force. Optionally, this embodiment comprises collecting this separated set of one or more cellular bodies. Thereafter, during a second part of this time period, a further set of one or more cellular bodies separate from the sample surface. This embodiment comprises collecting the further set of one or more cellular bodies. These are preferably collected separately from the set of one or more cellular bodies that separated during the first time period if these are collected at all. This embodiment allows to investigate the binding force characteristics of cellular bodies in terms of how long it takes, at a certain value of $\omega^2 r$, for particles to separate from the sample surface. Note for example that the further set of cellular bodies has already been experiencing the same centrifugal force for at least the first part of time period. Apparently, this further set of cellular bodies only separate from the sample surface if they have experienced a centrifugal force for some time period, i.e. for a time period that is longer than the above mentioned first part of the time period.

In an embodiment, the method comprises providing a first collecting surface in the holding space, the first collecting surface being configured to bind the separated first set of one or more cellular bodies, causing the separated first set of cellular bodies to be incident on the first collecting surface, providing a second collecting surface in the holding space, the second collecting surface being configured to bind the second set of one or more cellular bodies and causing the separated second set of cellular bodies to be incident on the second collecting surface.

In an embodiment of the system, the collection system comprises a first collecting surface configured to bind separated cellular bodies and a second collecting surface configured to bind separated cellular bodies, wherein the collection system is configured to provide the first collecting surface in the fluid medium for collecting a separated first set of one or more cellular bodies and to, thereafter, provide the second collecting surface in the fluid medium for collecting a separated second set of one or more cellular bodies.

These embodiments enable to separately collect the first and second set, and possibly even more sets, of one or more cellular bodies very easily. When the sample is rotating at $\omega_1^2 r_1$, then the first collecting surface may be provided and when the sample is rotating at $\omega_2 r_2$ the second collecting surface may be provided. Preferably, these collecting surfaces are both provided such that the centrifugal force drives separated cellular bodies towards the collecting surface, e.g. opposite the sample surface. Preferably, the second collecting surface, when the sample holder is rotating at $\omega_2^2 r_2$, is positioned at the same position with respect to the sample surface as the first collecting surface is when the sample holder is rotating at $\omega_1^2 r_1$. The second collecting surface may thus at some point replace the first collecting surface. It may be the case, particularly in a standard commercial bucket centrifuge, that a direction of centrifugal force with respect to the sample surface changes as a function of angular velocity ω. In that case it may be preferred that the position of the collecting surface is adjusted accordingly.

The collecting surfaces described herein are preferably perpendicular to the direction of the centrifugal force, e.g. are preferably perpendicular to a radial direction of the axis of rotation.

It should be appreciated that in an example of this method embodiment, the method comprises increasing the value of $\omega^2 r$ in a continuous manner, for example by keeping the distance r constant and monotonously increasing the angular velocity ω with respect to time. In an example of this system embodiment, the rotation provisioning system is configured to increase the value of $\omega^2 r$ in a continuous manner. It should be appreciated that in such embodiments $\omega^2 r$ will have in principle an infinite number of different values, thus will surely have two different values associated with two respective time instances. The above mentioned first value, $\omega_1^2 r_1$, and second value. $\omega_2^2 r_2$, may be understood to refer to such two different values in a continuous range of values.

The first collecting surface and second collecting surface may be different parts, e.g. different areas, of the same main collecting surface. A collecting surface as referred to herein may be a functionalized wall surface.

The step of causing the first/second set of particles to be incident at the first/second collecting surface can be performed by simply continuing to rotate the sample holder, e.g. at $\omega_1^2 r_1$ or $\omega_2^2 r_2$, so that the centrifugal force drives the separated cellular bodies towards the first/second collecting surface. In such case, preferably, the first/second collecting surface sits radially outwardly/inwardly (depending on the density of the fluid medium) from said sample surface.

In an embodiment, providing the first collecting surface and then the second collecting surface comprises moving, e.g. continuously moving, a main collecting surface with respect to said sample surface, the main collecting surface comprising the first collecting surface and the second collecting surface.

In an embodiment, the collection system is configured to move, e.g. continuously move, a main collecting surface with respect to said sample surface, the main collecting surface comprising the first collecting surface and the second collecting surface.

Preferably, the main collecting surface is moved in dependence on time or in dependence on the value for $\omega^2 r$. The collection system, in particular a data processing thereof, may for example be pre-programmed to move the main collecting surface in a predefined manner. Then, each region of the main collecting surface is associated with a certain time instance, namely with the time instance at which the region in question is positioned such that it can receive separated cellular bodies. Such time instance for example indicates the time period that has lapsed since the beginning of an experiment. Then, the value of $\omega^2 r$ may be varied and the value of $\omega^2 r$ at each time instance may be stored. This allows to associate each position of the main collecting surface with a value of $\omega^2 r$, for example to associate a first value $\omega_1^2 r^1$ with the first collecting surface within the main collecting surface and a second value $w_2^2 r_2$ with the second collecting surface within the main collecting surface.

In another example, the main collecting surface may be moved in dependence on the value for $\omega^2 r$. Then, each position on the main collecting surface is directly associated with a value for $\omega^2 r$.

Alternatively, the main collecting surface is stationary with respect to the sample surface and the method comprises directing respective sets of one or more separated cellular bodies to respective areas on the main collecting surface. In such case, the system may comprise a cellular body directing element that is configured to direct separated cellular bodies towards different areas on the main collecting surface. Similarly, when different reservoirs are used to collect different sets of one or more cellular bodies, these reservoirs may also be stationary with respect to the sample surface and the method may comprise directing respective sets of separated cellular bodies to respective reservoirs. In such case, the system may also comprise a cellular body directing element as described above. An example of such cellular body directing element that can direct separated cellular bodies in various directions is a movable funnel. Another example is a changeable acoustic field. For example a lateral force acoustic field as indicated in FIG. 9.

In an embodiment, the method comprises focusing the separated one or more cellular bodies in the fluid medium alter separation from the sample surface. In an embodiment, the system comprises a cellular body focusing system that is configured to focus the separated one or more cellular bodies in the fluid medium alter separation from the sample surface.

These embodiments enable to reduce the size of collecting parts of the collection system. To illustrate, focusing the cellular bodies after separation from the sample surface, e.g. when they are travelling through the fluid medium away from the sample surface, enables to direct the cellular bodies to a small region or area where they can be physically grouped. Focusing cellular bodies can for example be used to reduce the area of a collecting surface, in which area the cellular bodies are incident. This allows efficient usage of collecting surfaces. Such embodiments for example also enables to reduce the size of reservoir entrances.

Focusing separated cellular bodies may also increase the force resolution at which bodies can be separated. For example, a first group of cellular bodies released from an area of the sample surface, which area contacts, e.g. contains, the one or more cellular bodies prior to separation, without focusing may result in a similar area of collection on the collecting surface. In that case, depending on the translation speed of the collecting surface with respect to the sample surface, the collection area for a second group of bodies released at a later time may overlap considerably with the first collection area thereby not effectively separating first and second groups of cellular bodies. Focusing the cellular bodies after separation (at least focusing them in the direction of translation of the main collecting surface may prevent the overlap of the collection areas and thus improve the separation of the groups.

As used herein, focusing separated cellular bodies may be understood to refer to causing separated cellular bodies that are travelling away from the sample surface, to travel through a particular region within the sample holder, preferably within the holding space of the sample holder. The particular region may be defined as a two-dimensional area within the sample holder, for example as an area that is perpendicular to a vector that points radially outwards from the axis of rotation. Preferably, the particular region is relatively small, for example in the sense that it is a two-dimensional area as described above that is smaller than the surface area of the sample surface, which surface area contacts, e.g. contains, the one or more cellular bodies prior to separation. Causing separated cellular bodies to travel through such particular region may be achieved by applying further one or more forces to the separated cellular bodies to direct them to the particular region. Such further one or more forces are for example acoustic forces. In another example, such one or more further forces are applied by one or more physical surfaces of a cellular body focusing element, such as a physical funnel.

In an embodiment, focusing the separated one or more cellular bodies comprises causing the separated one or more cellular bodies to travel through a physical cellular body focusing element, such as a physical funnel, in the sample holder. In an embodiment of the system, the sample holder comprises the cellular body focusing system, wherein the cellular body focusing system comprises a physical cellular body focusing element, such as a physical funnel, for focusing the separated cellular bodies.

These embodiments provide a simple manner for focusing separated cellular bodies. The physical cellular body focusing element is preferably positioned between the sample surface and the collecting surface in question, e.g. the first or second collecting surface.

In an embodiment of the method, focusing separated cellular bodies, such as the separated first and/or second set of one or more cellular bodies, comprises generating an acoustic wave in the holding space. In an embodiment of the system, the cellular body focusing system comprises an acoustic wave generator that is configured to generated an acoustic wave in the holding space.

The acoustic wave preferably exerts a force on separated cellular bodies that directs them through a particular region or area in the holding space.

The acoustic wave generator may comprise or be a bulk acoustic wave generator to generate a bulk acoustic wave in the holding space and/or in a sample contained therein. The acoustic wave generator may be the acoustic wave generator as disclosed in WO 2018/083193.

In an embodiment, the one or more cellular bodies prior to separation from said sample surface span a particle containing area on said sample surface. In such embodiment, the method comprises focusing the separated first set of one or more cellular bodies in the fluid medium so that they are incident on a first area of the first collecting surface, wherein the first area is smaller than the particle containing area on said sample surface, and focusing the separated second set of one or more cellular bodies in the fluid medium so that they are incident on a second area of the second collecting surface, wherein the second area is smaller than the particle containing area on said sample surface.

In an embodiment of the system, the physical cellular body focusing element is configured to perform such focusing of the first and second set of one or more cellular bodies.

These embodiments enable to efficiently use the collecting surfaces as also explained above.

In an embodiment, the method comprises collecting the first set of one or more cellular bodies in a first reservoir and collecting the second set of one or more cellular bodies in a second reservoir different from the first reservoir. Preferably, this embodiment also comprises focusing the first and second set of one or more cellular bodies as described above.

In an embodiment of the system, the collection system comprises a first reservoir for collecting the first set of one or more cellular bodies and a second reservoir for collecting the second set of one or more cellular bodies. Preferably, this embodiment also comprises a cellular body focusing system as described above.

These embodiments enable to separately collect the separated first and second set of one or more cellular bodies. Using reservoirs obviates the need to prepare collecting surfaces for collecting cellular bodies.

The method according to the preceding claim, wherein the step of collecting the first set of one or more cellular bodies in a first reservoir comprises closing of the first reservoir using a first barrier. Optionally, the step of collecting the second set of one or more cellular bodies in the second reservoir comprises closing of the second reservoir using a second barrier. Then, preferably, the first barrier functions as a barrier for keeping the cellular bodies within the second reservoir.

In an embodiment of the system, the collection system is configured to close off a first reservoir using a first barrier for collecting a separated first set of one or more cellular bodies, and, optionally, to close off a second reservoir using a second barrier for collecting a separated second set of one or more cellular bodies. Preferably, the first barrier functions as a barrier for keeping the cellular bodies within the second reservoir. Preferably, this embodiment also comprises a cellular body focusing system as described above.

These embodiments are advantageous in that no functionalized wall surfaces are required and in that the same barrier is used for forming both the first and the second reservoir, which is an efficient usage of material.

In an embodiment, the method comprises collecting the first set of one or more cellular bodies in a first reservoir comprising closing of the first reservoir using a first barrier, and providing a collecting surface in the holding space, the collecting surface being configured to bind the second set of one or more cellular bodies and causing the separated second set of cellular bodies to be incident on the second collecting surface.

In this embodiment, preferably, the collecting surface is provided on the first barrier. Then, the collecting surface is automatically provided when the first reservoir is closed by the first barrier.

In an embodiment of the system the collection system is configured to close off a first reservoir using a first barrier for collecting the separated first set of one or more cellular bodies in the first reservoir and to provide a collecting surface in the holding space, the collecting surface being configured to bind the second set of one or more cellular bodies. In this embodiment, preferably, the collecting surface is provided on the first barrier. Then, the collecting surface is automatically provided when the first reservoir is closed by the first barrier.

The method according to any of the preceding claims, comprising removing the collected one or more cellular bodies from the sample holder, e.g. from the holding space, and analyzing the thus obtained one or more cellular bodies. The obtained collected cellular bodies may, for example, be analyzed using light-absorption measurements, e.g. UV-absorption measurements, or by simply counting them using a microscope, which allows for very accurate avidity analyses as shown in FIG. 10.

Removing collected cellular bodies from the sample holder may simply be performed by removing one or more collecting surfaces to which cellular bodies are bound, from the sample holder, in particular from the holding space, and/or removing one or more reservoirs containing separated cellular bodies, from the sample holder.

Analyzing the obtained one or more cellular bodies for example comprises determining at which collecting surfaces they are present, or in which reservoirs, in order to assess at which value of $\omega^2 r$ they separated from the sample surface.

One aspect of this disclosure relates to a method for detecting one or more cellular bodies in dependence on their binding force with a sample surface, the method comprising providing a sample holder comprising a holding space, wherein the holding space comprises, e.g. is substantially filled with, a fluid medium and comprises the sample surface and the one or more cellular bodies in the fluid medium, wherein the one or more cellular bodies are contacting said sample surface, and rotating the sample holder around an axis of rotation for causing a centrifugal force on the one or more cellular bodies herewith separating the one or more cellular bodies from the sample surface, and focusing the separated one or more cellular bodies in the fluid medium after separation from the sample surface and detecting the separated one or more cellular bodies in the fluid medium after they have been separated from the sample surface, preferably while the separated one or more cellular bodies are moving through the fluid medium.

One aspect of this disclosure relates to a system for detecting one or more cellular bodies in dependence on their binding force with a sample surface, the system comprising a sample holder comprising a holding space for holding the sample surface, a fluid medium and the one or more cellular bodies in contact with the sample surface, a rotation provisioning system configured to rotate the sample holder around an axis of rotation for causing a centrifugal force on the one or more cellular bodies for separating the one or more cellular bodies from the sample surface, and a cellular body focusing system that is configured to locus the separated one or more cellular bodies in the fluid medium after separation from the sample surface, and a detection system for detecting the separated one or more cellular bodies in the fluid medium after they have been separated from the sample surface, preferably while the separated one or more cellular bodies are moving through the fluid medium.

Such method and system are highly advantageous in that they enable to accurately detect and thus count separated cellular bodies. Such detection is namely more accurate if the cellular bodies pass through a small area or region in the holding space or sample holder.

As explained above, focusing separated cellular bodies may be understood to cause the separated cellular bodies to flow through a certain limited area or volume. Preferably, the cellular bodies are detected as they travel through such area or volume. This improves the accuracy with which separated cellular bodies can be detected. As used herein, cellular bodies travelling through an area or volume may be understood to refer to the cellular bodies at some point in time entering said volume or area and at a later point in time exiting said volume or area. Preferably, the cellular bodies do not stop and/or do not accumulate in such area or volume. This allows the accurately detect each individual cellular body that passes by.

It should be appreciated that the method for detecting cellular bodies may comprise any of the steps that are comprised in any method for collecting cellular bodies as described herein, such as steps of collecting cellular bodies, focusing cellular bodies, et cetera. It should be appreciated that the system for detecting cellular bodies may comprise any of the elements that are comprised by any system for collecting cellular bodies as described herein, such as a collection system as described herein, a cellular body focusing element as described herein, et cetera.

To illustrate, the method for detecting one or more cellular bodies may comprise rotating the sample holder at a first angular velocity, $\omega_1$, the sample surface being positioned a distance, $r_1$, from the axis of rotation, $\omega_1^2 r_1$ having a first value, for causing a centrifugal force on the one or more cellular bodies herewith separating the first set of one or more cellular bodies from the sample surface, and rotating the sample holder at a second angular velocity, $\omega_2$, the sample surface being positioned a distance, $r_2$, from the axis of rotation, $\omega_2^2 r_2$ having a second value different from, preferably higher than, said first value, for causing a centrifugal force on one or more cellular bodies still contacting the sample surface herewith separating the second set of one or more cellular bodies from the sample surface. The first and second set of cellular bodies are then focused and detected. Preferably a method would linearly or monotonically increase $\omega^2 r$ as a function of time (e.g. to create a force ramp) either continuously or in a stepwise manner, and detect separating cellular bodies also as a function of time.

One aspect of this disclosure relates to a computer-implemented method comprising the steps of causing a rotation provisioning system to, at a first time instance $t_1$, rotate a sample holder around an axis of rotation at $\omega_{t1}^2 r_{t1}$, the sample holder comprising a holding space for holding a sample surface, a fluid medium and one or more cellular bodies in contact with the sample surface, wherein $\omega_{t1}$ indicates the angular velocity of the rotation of the sample holder at the first time instance and $r_{t1}$ indicates a distance at the first time instance between the sample surface and the axis of rotation, wherein the rotation of the sample holder at $\omega_{t1}^2 r_{t2}$ suitable for causing a centrifugal force on the one or more cellular bodies for separating a first set of one or more cellular bodies from the sample surface. The computer-implemented further comprises causing the rotation provisioning system to, at a second time instance $t_2$, rotate the sample holder at $\omega_{t2} r_{t2}$ wherein $\omega_{t2}$ indicates the angular velocity of the rotation of the sample holder at the second time instance and $r_{t2}$ indicates a distance at the second time instance between the sample surface and the axis of rotation, wherein the rotation of the sample holder at $\omega_{t2}^2 r_{t2}$ is suitable for causing a centrifugal force on the one or more cellular bodies for separating a second set of one or more cellular bodies from the sample surface. The computer-implemented further comprises causing a collection system for collecting the separated cellular bodies to provide at the first time instance a first collecting surface or first reservoir in the fluid medium for collecting the separated first set of one or more cellular bodies and to, at the second time instance, provide a second collecting surface or second reservoir in the fluid medium for collecting the separated second set of one or more cellular bodies.

Causing the value of $\omega^2 r$ to change may involve causing the angular velocity $\omega$ to change and/or to causing the distance r to change. It should be appreciated that $\omega_{t1}^2 r_{t1}$ and $\omega_{t2}^2 r_{t2}$ may be equal or different.

In an embodiment, the step of causing the collection system to provide the first and second collecting surface comprises causing the collection system to move, e.g. to continuously move, a main collecting surface with respect to said sample surface, the main collecting surface comprising the first collecting surface and the second collecting surface.

In an embodiment, the computer-implemented method comprises storing $\omega_{t1}^2 r_{t1}$ in association with the first collecting surface and $\omega_{t2}^2 r_{t2}$ in association with the second collecting surface.

This embodiment enables to accurately analyze the first and second set of cellular bodies in that it can be accurately assessed at which $\omega^2 r$ values, or at which time instances (see below), they separated from the sample surface.

Storing a value of $\omega^2 r$ may be performed by separately storing the respective values of $\omega$ and r, so that the calculation of $\omega^2 r$ can be performed at any time.

Preferably, the embodiment also comprises storing $\omega_{t1}^2 r_{t1}$ in association with the first time instance and $\omega_{t2}^2 r_{t2}$ in association with the second time instance. In fact, in an embodiment, the time instance is the link between a value of $\omega^2 r$ and a particular collecting surface. In such embodiment, the time-course for $\omega^2 r$ should be monitored and which collecting surface, or which part, is provided for collecting separated cellular bodies at which time instances.

It should be appreciated that any step of causing the rotation provisioning system and/or collection system to perform a step may be simply performed by sending an appropriate control signal to the rotation provisioning system and/or collection system, respectively.

One aspect of this disclosure relates to a data processing system that is configured to perform any of the computer-implemented methods described herein.

Any of the systems described herein, for example the system for collecting cellular bodies or the system for detecting cellular bodies may comprise a data processing system that is configured to control the system such that it performs any of the methods described herein. These systems for example comprise the data processing system as described above.

One aspect of this disclosure relates to a computer program comprising instructions which, when the program is executed by a data processing system, cause the data processing system to carry out any of the computer-implemented methods described herein.

One aspect of this disclosure relates to a non-transitory computer-readable storage medium storing at least one software code portion, the software code portion, when executed or processed by a computer, is configured to perform any of the methods described herein.

One aspect of this disclosure relates to a computer program or suite of computer programs comprising at least one software code portion or a computer program product storing at least one software code portion, the software code portion, when run on a computer system, being configured for executing any of the methods described herein.

One aspect of this disclosure relates to a computer comprising a a computer readable storage medium having computer readable program code embodied therewith, and a processor, preferably a microprocessor, coupled to the computer readable storage medium, wherein responsive to executing the computer readable program code, the processor is configured to perform any of the methods described herein.

As will be appreciated by one skilled in the art, aspects of the present invention may be embodied as a system, a method or a computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Functions described in this disclosure may be implemented as an algorithm executed by a processor/microprocessor of a computer. Furthermore, aspects of the present invention may take the form of a computer program product embodied in one or more computer readable medium(s) having computer readable program code embodied, e.g., stored, thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples of a computer readable storage medium may include, but are not limited to, the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of the present invention, a computer readable storage medium may be any tangible medium that can contain, or store, a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber, cable, RF, etc., or any suitable combination of the foregoing. Computer program code for carrying out operations for aspects of the present invention may be written in any combination of one or more programming languages, including an object oriented programming language such as Java™, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer, or entirely on the remote computer or server. In the latter scenario, the remote computer may be connected to the users computer through any type of network, including a local area network (LAN) or a wide area network (WAN), or the connection may be made to an external computer (for example, through the Internet using an Internet Service Provider).

Aspects of the present invention are described below with reference to flowchart illustrations and/or block diagrams of methods, apparatus (systems), and computer program products according to embodiments of the present invention. It will be understood that each block of the flowchart illustrations and/or block diagrams, and combinations of blocks in the flowchart illustrations and/or block diagrams, can be implemented by computer program instructions. These computer program instructions may be provided to a processor, in particular a microprocessor or a central processing unit (CPU), of a general purpose computer, special purpose computer, or other programmable data processing apparatus to produce a machine, such that the instructions, which execute via the processor of the computer, other programmable data processing apparatus, or other devices create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in the figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function (s). It should also be noted that, in some alternative implementations, the functions noted in the blocks may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustrations, and combinations of blocks in the block diagrams and/or flowchart illustrations, can be implemented by special purpose hardware-based systems that perform the specified functions or acts, or combinations of special purpose hardware and computer instructions.

Moreover, a computer program for carrying out the methods described herein, as well as a non-transitory computer readable storage-medium storing the computer program are provided. A computer program may, for example, be downloaded (updated) to the existing data processing systems (e.g. to the existing or be stored upon manufacturing of these systems.

Elements and aspects discussed for or in relation with a particular embodiment may be suitably combined with elements and aspects of other embodiments, unless explicitly stated otherwise. Embodiments of the present invention will be further illustrated with reference to the attached drawings, which schematically will show embodiments according to the invention. It will be understood that the present invention is not in any way restricted to these specific embodiments.

BRIEF DESCRIPTION OF THE DRAWINGS

Aspects of the invention will be explained in greater detail by reference to exemplary embodiments shown in the drawings, in which.

DETAILED DESCRIPTION OF THE DRAWINGS

In the figures, identical reference numbers indicate identical or similar elements.

Figure 1:
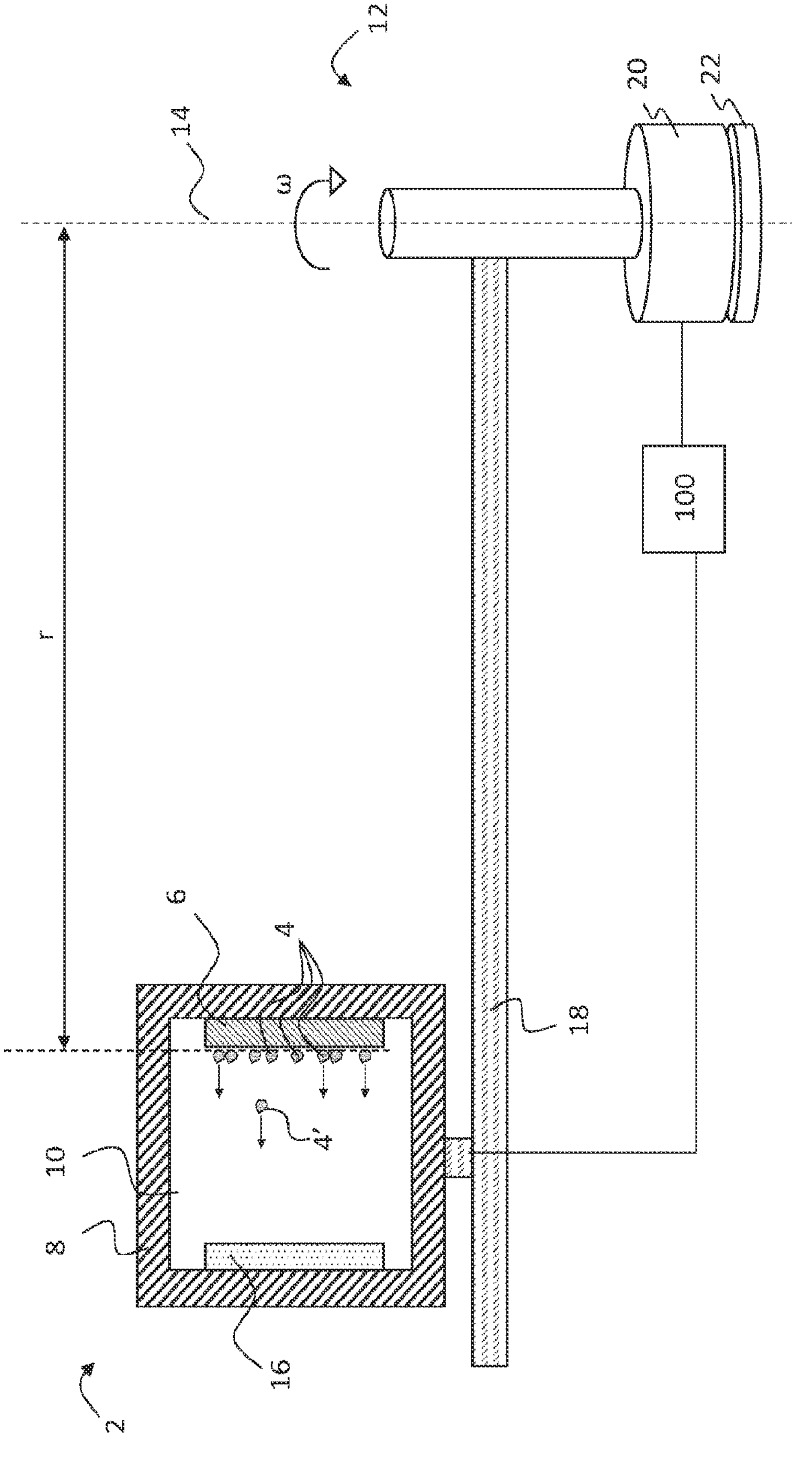
FIG. 1 schematically illustrates a system according to an embodiment.

FIG. 1 schematically illustrates a system 2 for collecting one collecting one or more cellular bodies 4 in dependence on their binding force with a sample surface 6. The one or more cellular bodies 4 may be bound to the sample surface 6. Sample surface 6 may be a functionalized wall surface that has been prepared with material that binds the one or more cellular bodies 4. In an example, the one or more cellular bodies are immune cells and the sample surface 6 may have been prepared with target cells or with ligands that bind to receptors on these immune cells. The cellular bodies may be one or more biological cells. The system 2 further comprises a sample holder 8 that comprises a holding space 10 for holding the sample surface 6, a fluid medium, and the one or more cellular bodies 4 in contact with the sample surface 6. The fluid medium may be any medium through which the separated cellular bodies can move after they have been separated from the sample surface. An example of a fluid medium is a cell medium, e.g. RPMI. Other suitable fluids are liquids and gels, e.g. water, watery fluids, biocompatible solvents, oils, gels, hydrogels and bodily fluids. The system 2 also comprises a rotation provisioning system 12 configured to rotate the sample holder 8 around an axis of rotation 14 for causing a centrifugal force on the one or more cellular bodies 4 for separating the one or more cellular bodies from the sample surface 6. The system 2 further comprises a collection system 16 for collecting the separated cellular bodies 4'.

The one or more cellular bodies 4 are preferably provided on the sample surface 6 before the sample surface is positioned in the holding space or at least before the sample holder is placed on the rotation provisioning system.

A functionalised wall surface as referred to herein may be provided with one or more primers. The primers may comprise one or more types of interaction moieties. In particular a functionalised wall surface may be provided with one or more substances comprising at least one of antibodies, peptides, biological tissue factors, biological tissue portions, bacteria, antigens, proteins, ligands, cells, tissues, viruses, (synthetic) drug compounds, lipid (bi)layers, fibronectin, cellulose, nucleic acids, RNA, small molecules, allosteric modulators, (bacterial) biofilms, "organ-on-a-chip", etc., and/or specific atomic or molecular surface portions (e.g. a gold surface) to which at least part of the cellular bodies tends to adhere with preference relative to other surfaces.

Optionally, the system comprises a data processing system that is configured to control the system 2, in particular to control the rotation provisioning system 12. The data processing system may be configured to control the angular velocity ω with which the sample holder 8 rotates around axis of rotation 14. The data processing system 100 may also be configured to control the distance r between the sample surface 6 and axis 14.

In the depicted embodiment, the rotation provisioning system 14 comprises a rotary arm 18 that is mounted onto a rotor system that includes a rotor 20 and a rotary joint 22. Further, the sample holder 8 is mounted onto the rotary arm 18. The sample holder 8 may be translatable over rotary arm 18 in order to control the distance r.

Upon rotation of the sample holder around axis of rotation 14, the one or more cellular bodies 4 in contact with the sample surface experience a centrifugal force F, which is approximately given for each cellular body as: $F=m\omega^2 r$, wherein m indicates a mass of the cellular body, ω indicates the angular velocity of the rotation and r indicates the distance between axis of rotation and the sample surface. Due to the centrifugal force, the cellular bodies thus experience a force. The sign of the force experienced by the cellular bodies depends on the orientation of the sample surface 6 with respect to the rotation axis 14. Since the fluid medium also experiences a centrifugal force, a resulting force on the cellular bodies also depends on the density of the cellular bodies with respect to the fluid medium. For the geometry sketched in FIG. 1 cellular bodies with a density higher than that of the fluid medium will experience a force away from the sample surface 6. If this force becomes higher than the binding force associated with a bond between a cellular body and sample surface, the cellular body is separated from the sample surface 6. Such centrifugal force may cause bond rupture and as such separation of the cellular body from the sample surface 6.

The separated cellular bodies 4' due to the still present centrifugal force are driven away from the sample and are subsequently collected using a collection system 16. As used herein, such collecting may be understood to relate to physically grouping together the separated set of one or more cellular bodies in a certain volume or area. Preferably no other cellular bodies are in that volume or area so that the separated set of cellular bodies can be obtained and analyzed separately. Preferably, the collected one or more cellular bodies are removed from the sample holder and subsequently analyzed. Such collected cellular bodies can also be further processed, such as sequenced together.

For example, the cellular bodies may be cells and the collection sample surface may be coated with specific ligands that promote cell adhesion. This may facilitate collection of the released cellular bodies after stopping the centrifuge by collecting the collection sample surface. The cellular bodies may for example be removed from the functionalized collection sample surface by adding an agent inhibiting the cell-ligand interaction for further downstream analysis or use. The cellular bodies may also be analyzed, (e.g. simply quantified by counting or by fluorescence or other optical measurement), directly on the collection surface.

The collection system may comprise a collecting surface 16, which may be a functionalized wall surface that is configured to bind separated cellular bodies 4'. As such, the collecting surface 16 may be said to have a sticky sample surface for the cellular bodies. In another embodiment, the collection system comprises one or more collection tubes, or reservoirs. Such tubes and reservoirs may be advantageous in that they do not require sticky sample surfaces.

Optionally, the system 2 comprises a microscope that is installed on the rotary arm 18 for observing the sample (not shown).

Figure 2A:
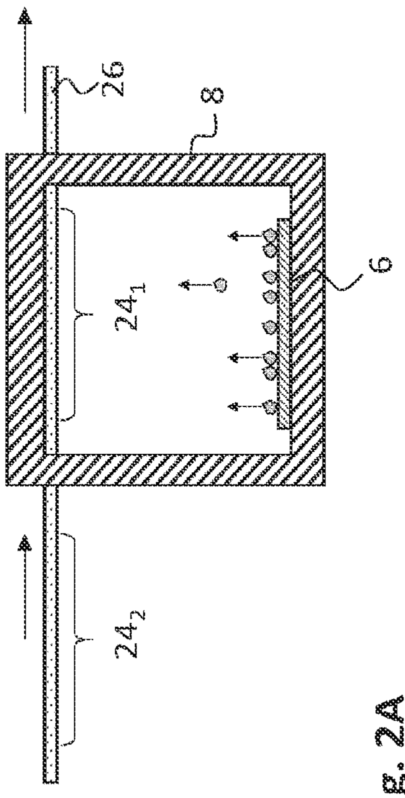
FIGS. 2A-2C illustrate embodiments wherein a movable main collecting surface is used for collecting different sets of one or more cellular bodies.

FIG. 2A illustrates an embodiment wherein providing different collecting surfaces for collecting different sets of cellular bodies comprises moving, for example continuously moving, a main collecting surface 26 with respect to the sample surface 6. The depicted main collecting surface 26 comprises first collecting surface $\mathbf{24}_1$ and second collecting surface $\mathbf{24}_2$.

The data processing system 100 that is optionally present in the system 2 may be configured to perform a step of causing the rotation provisioning system 14 to, at a first time instance $t_1$, rotate sample holder 8 around an axis of rotation 14 at $\omega_{t1}^2 r_{t1}$. Due to this rotation a first set of one or more cellular bodies may be separated from the sample surface 6. The data processing system 100 may further be configured to perform a step of causing the rotation provisioning system 14 to, at a second time instance $t_2$, rotate the sample holder at $\omega_{t2}^2 r_{t2}$, Due to this rotation a second set of one or more cellular bodies may be separated from the sample surface 6. The data processing system is further configured to perform a step of causing a collection system 16 to provide at the first time instance a first collecting surface $\mathbf{24}_1$ in the fluid medium for collecting the separated first set of one or more cellular bodies and to, at the second time instance, provide a second collecting surface $\mathbf{24}_2$ in the fluid medium for collecting the separated second set of one or more cellular bodies.

Preferably, the data processing system stores the respective values for $\omega^2 r$ that are used during an experiment in association with the respective collecting surfaces that were provided when these values were used. Thus, with reference to FIG. 3B, the data processing system would store $\omega_1^2 r_1$ in association with the first collecting surface $\mathbf{24}_1$ and $\omega_2^2 r_2$ in association with the second collecting surface $\mathbf{24}_2$, et cetera.

Figure 2B:
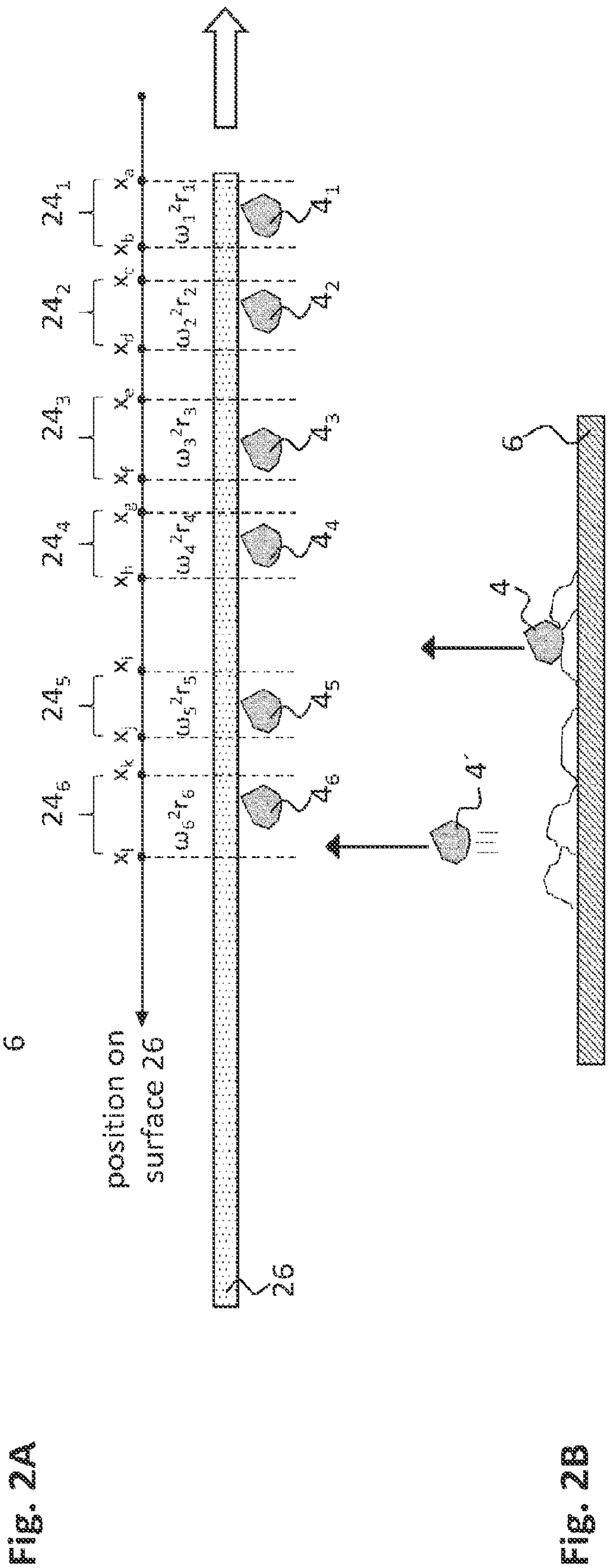

FIG. 2B illustrates that many more sets $\mathbf{4}_x$ of cellular bodies can be collected by providing many different collecting surfaces $\mathbf{24}_x$ subsequently. All these collecting surfaces 24*x* may be respective areas on the same main collecting surface 26.

By moving the collection sample surface 26 with respect to the sample surface 6 the time and/or force at which separation from the sample surface 6 occurred may be encoded by a spatial location on the collection sample surface 26. In FIG. 2B, by moving the collection sample surface 26 to the right with respect to the sample surface 6 the cellular bodies that released at force $\omega_1^2 r_1$ ends up on the right hand side of the collection sample surface 26, namely at collection sample surface $\mathbf{24}_1$ while cellular bodies which release at higher values of $\omega^2 r$ end up in collection sample surfaces displaced to the left with respect to collection sample surface $\mathbf{24}_1$. In this example $\omega_1^2 r_1<\omega_2^2 r_2<\omega_3^2 r_3<\omega_4^2 r_4<\omega_5^2 r_5<\omega_6^2 r_6$.

Figure 2C:
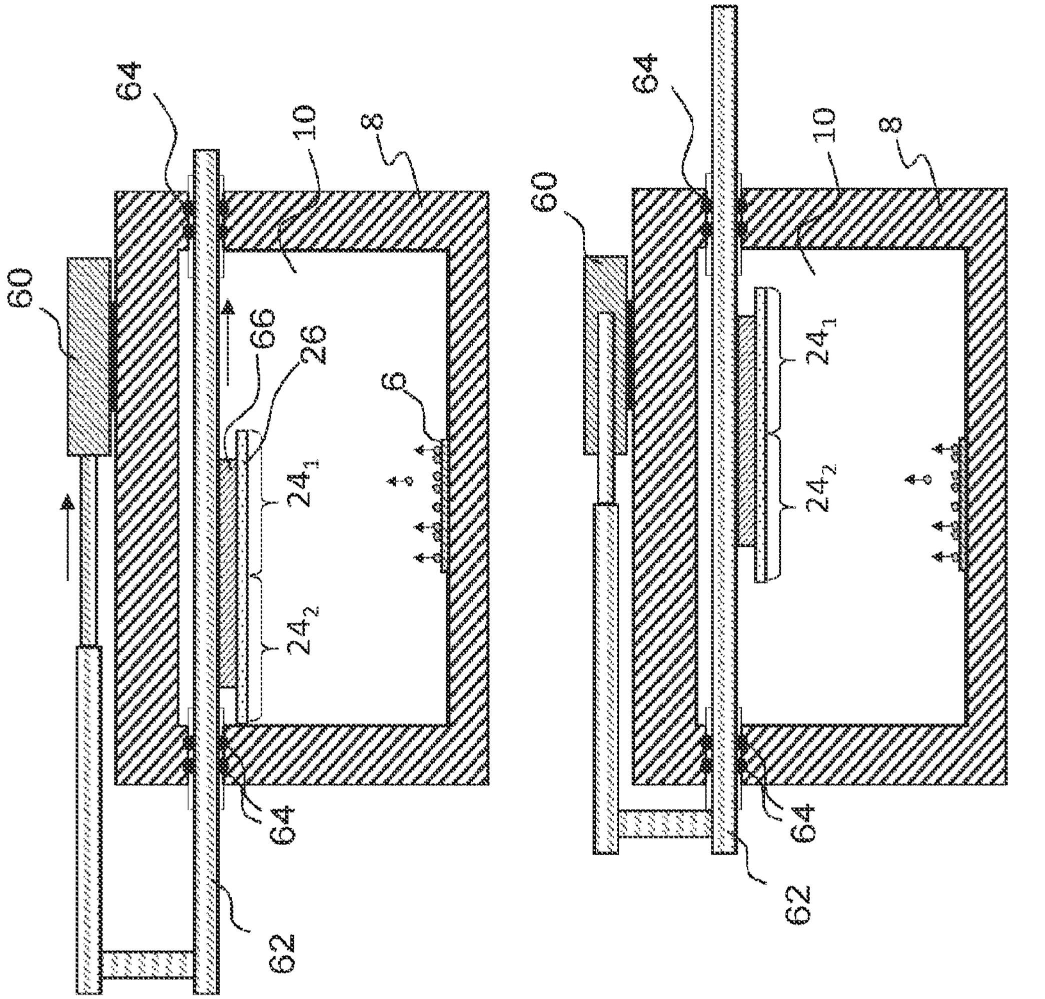

FIG. 2C illustrates an embodiment wherein a main collecting surface 26, which comprises collecting surface $\mathbf{24}_1$ and collecting surface $\mathbf{24}_2$, is moved relative to sample surface 6, as indicated by the arrows. This movement causes that first collecting surface $\mathbf{24}_1$ is positioned opposite the sample surface 6, and then collecting surface $\mathbf{24}_2$ is positioned opposite the sample surface 6. The top figure indicates the situation at a first time instance, and the bottom figure indicates the situation at a later time instance, after the main collecting surface 26 has moved relative to the sample surface 6.

In the depicted embodiment, a linear actuator 60 connected to the controller 100 (not shown) can be used to translate a pushrod 62 which runs through the holding space 10. The pushrod 62 is rigidly connected to the main collecting surface 26 which follows the motion of the push rod 62. A support 66 for the main collecting surface 26 may be directly connected to the push rod 62 or, in order to provide more rigid support, two push rods may be used side-by-side. Alternatively, the main collecting surface 26 may be supported from the sides by guiding rails in the holding space for ensuring that the orientation of the main collecting surface 26 remains the same relative to sample surface 6, e.g. parallel to sample surface 6. The entry and exit in the holding space for the pushrod may be sealed, e.g. using o-ring seals or t-seals 64, for preventing fluid medium to leak out of the holding space. The holding space 10 may comprise a detachable cap (not shown) to facilitate loading and removal of sample 6 and the collection surfaces and the fluid medium.

Figure 3B:
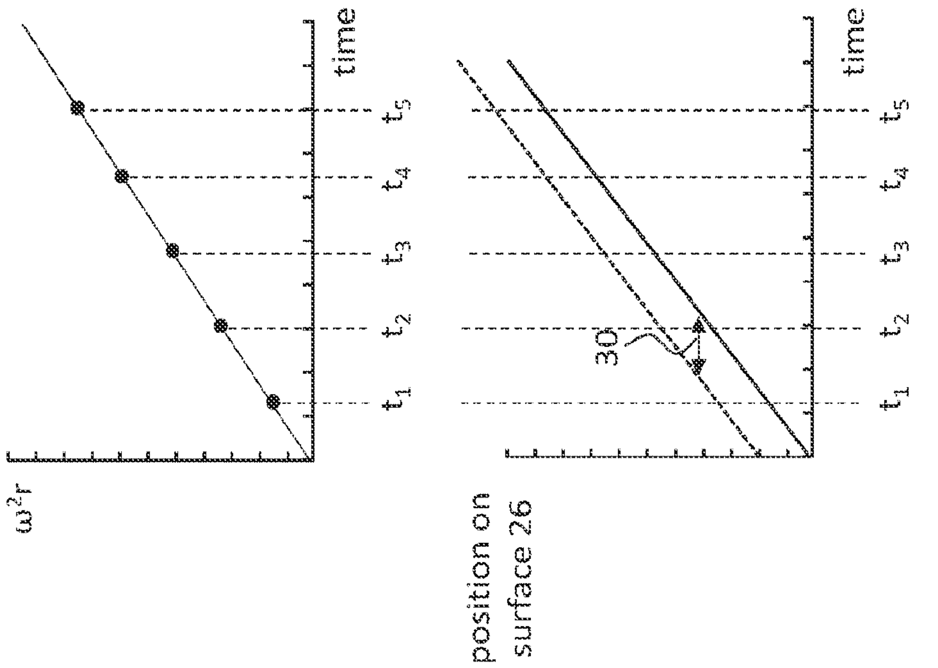
FIG. 3B illustrates an embodiment wherein the sample holder is rotated at monotonously increasing value for $\omega^2 r$ and wherein the main surface is moved continuously.
Figure 3A:
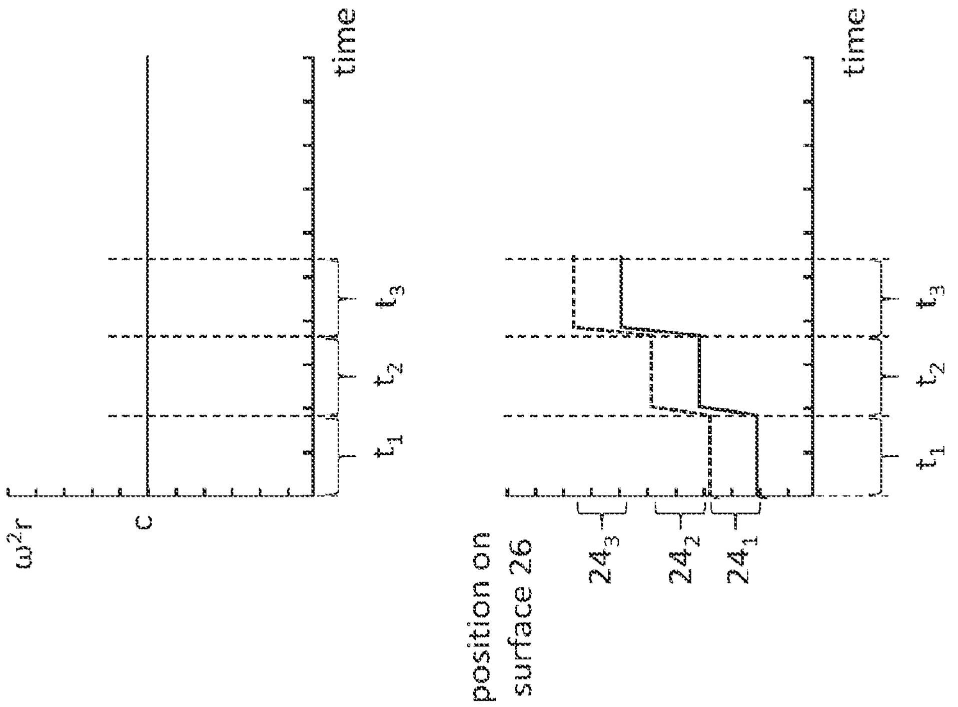
FIG. 3A illustrates an embodiment wherein the sample holder is rotated at a constant value for $\omega^2 r$ and wherein the main surface is moved in a step-wise manner.
Figure 3D:
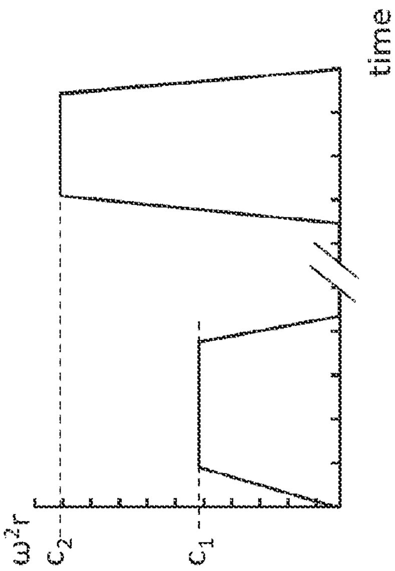
FIG. 3D illustrates an embodiment wherein first the sample holder is rotated at a first value of $\omega^2 r$ and then at a second value, higher than the first value.
Figure 3C:
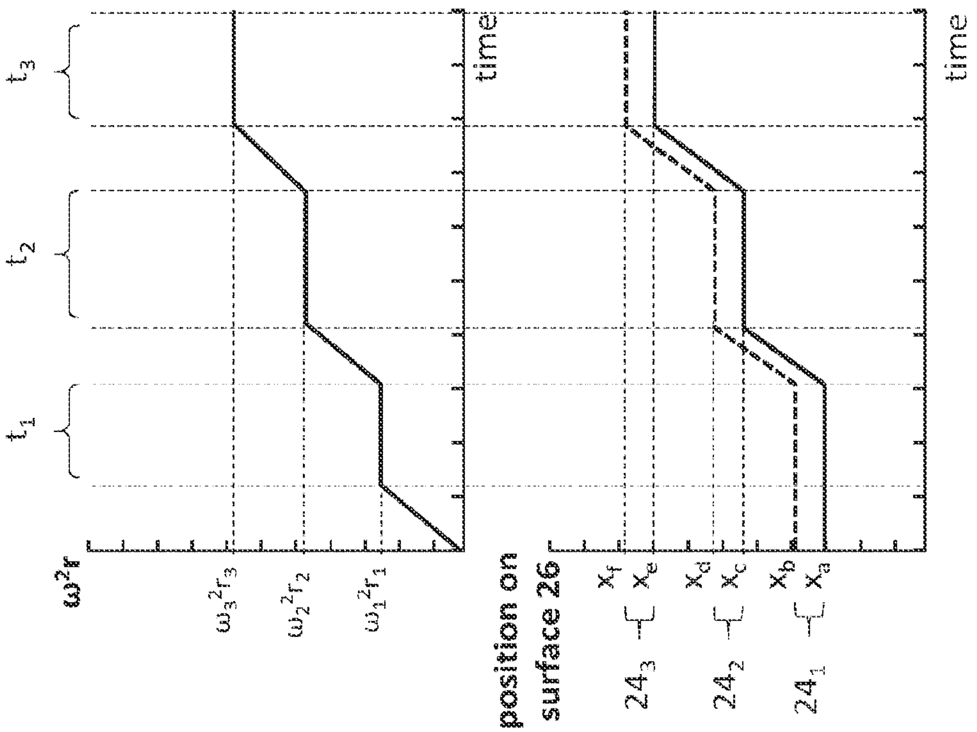
FIG. 3C illustrates an embodiment wherein the value for $\omega^2 r$ is increased incrementally and wherein the main surface is moved in a step-wise manner.

The bottom graphs of FIGS. 3A, 3B, 3C each indicates which part of a main collecting surface 26 is actively used as collecting surface during which time period. In the following, the active area of main collecting surface 26 at a particular point in time refers to the area that, at that particular point in time, can receive separated cellular bodies, for example because it is positioned opposite the sample surface 6. In each bottom graph of FIGS. 3A, 3B, 3C, the solid line indicates the position on sample surface 26 of a right boundary of the active area and the dashed line indicates a left boundary of the active area. Thus, at any point in time, the vertical distance between the solid line and dashed line may be understood to indicate the area of main collecting surface 26 that possibly collects separated cellular bodies, i.e. may be understood to indicate the active area.

FIG. 3A illustrates an embodiment wherein the sample holder 8 is rotated at a constant value c for $\omega^2 r$ for some period. This time period comprises the time periods $t_1$, $t_2$, $t_3$. In the embodiment of FIG. 3A, during time period $t_1$, a first collecting surface $\mathbf{24}_1$, is active, for collecting separated cellular bodies that separate in period $t_1$ (see bottom graph of FIG. 3A). Similarly, a second collecting surface $\mathbf{24}_2$ is provided in time period $t_2$, a third collecting surface $\mathbf{24}_3$ in time period $t_3$. Thus, depending on when cellular bodies become separated from the sample surface 6 due to the rotation of the sample holder, they will be collected in different areas $\mathbf{24}_x$ on a main collecting surface 26. This allows to analyze which cellular bodies separate from the sample surface only after a force has been applied to them for a longer time period.

FIG. 3B illustrates a similar embodiment as in FIG. 2A with the difference that $\omega^2 r$ increases, e.g. is ramped up, with time. In an example, $\omega^2 r$ increases in a continuous manner, for example in a linear manner. In such embodiment, depending at which value for $\omega^2 r$ the cellular bodies separate from the sample surface, they are collected in different areas of main collecting surface 26. Also, in this embodiment, the main collecting surface is moved continuously with respect to sample surface 6 (see the bottom graph of FIG. 3B). Such embodiment may be understood to make use of overlapping collecting areas in that each position of the main collecting surface 26 is associated with a time period indicated by arrow 30.

It should be appreciated that $\omega^2 r$ may be increased as depicted in the top graph of FIG. 3B, while the main collecting surface 26 is moved in accordance with the bottom graph of FIG. 3A. In such case, each collecting surface is associated with a value range for $\omega^2 r$.

FIG. 3C illustrates an embodiment, wherein $\omega^2 r$ is increased in a stepwise manner and wherein the main collecting surface 26 is also moved with respect to the sample surface 6 in a stepwise manner. FIG. 3C may be understood to depict the embodiment of FIG. 2B. Note that the positions $x_a$-$x_F$ are indicated both in FIG. 2B and in FIG. 3C.

FIG. 3D illustrates an embodiment wherein during a first time period, the sample holder is rotated at a value $c_1$ for $\omega^2 r$. As a result, a first set of one or more cellular bodies may separate from the sample surface. This set may not be of interest and is optionally discarded, i.e. not collected, for example by dismounting the sample holder 8 from the rotation provisioning system 14 and flushing the separated first set of one or more cellular bodies out of the holding space 10. Then, during a second time period, the sample holder is rotated at a value $c_2$ for $\omega^2 r$ in order to separate a second set of one or more cellular bodies from the sample surface 6. This second set may then be collected using a collection system as described herein. Hence, this embodiment allows to only collect cellular bodies that separate at a particular value of Or apart from cellular bodies that separate at values of $\omega^2 r$ that are lower than said particular value.

Note that the embodiment of FIG. 3D does not require any spatial encoding of time or $\omega^2 r$ on a collecting surface.

Figure 4:
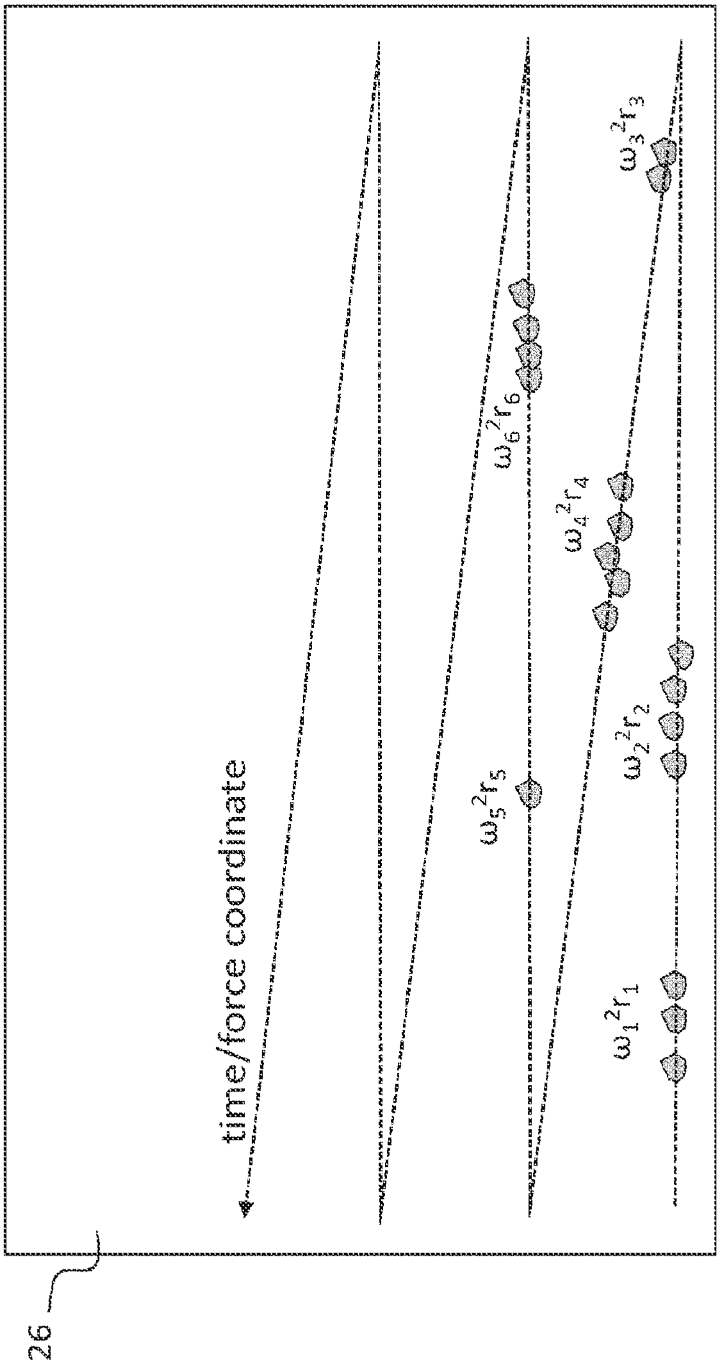
FIG. 4 illustrates an embodiment wherein the main collecting surface is moved in two dimensions with respect to the sample surface.

FIG. 4 illustrates an embodiment wherein the main collecting surface 26 is moved in two dimensions with respect to the sample surface, in particular in a raster or zig-zag manner. Each area of the main collecting surface is associated with an $\omega^2 r$ value. It should be appreciated that different areas of the main collecting surface 26 may be associated with the same $\omega^2 r$ value. To illustrate $\omega_6{}^2 r_6$ and $\omega_3{}^2 r_3$ may be equal.

Figure 5:
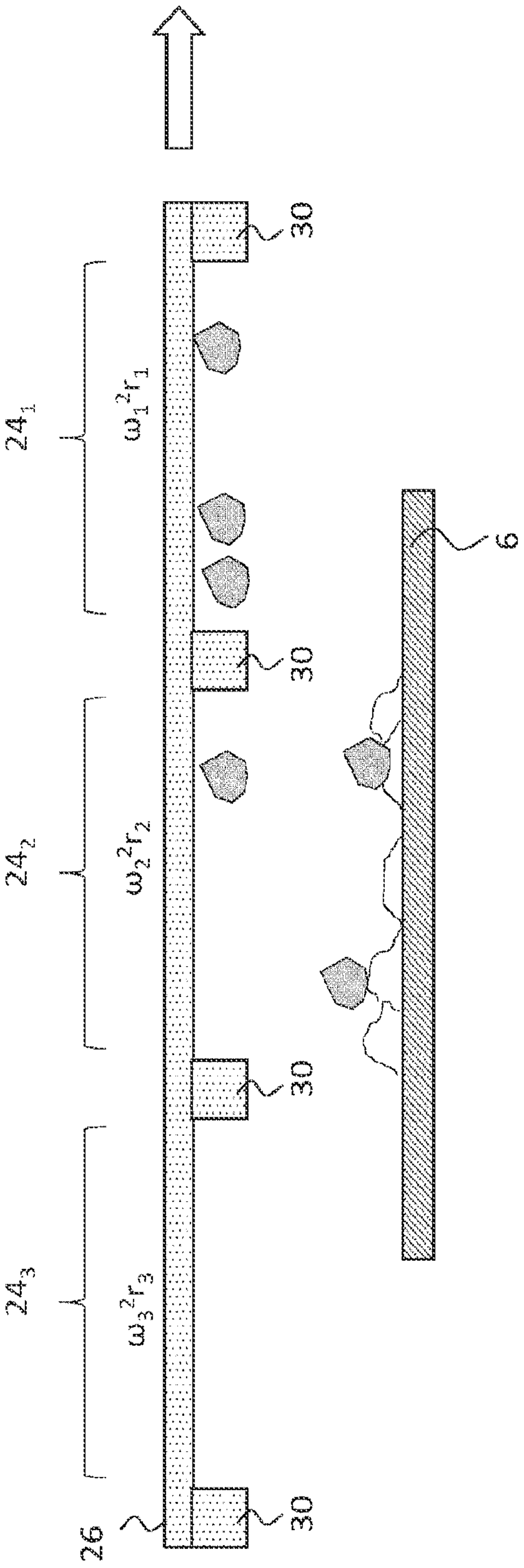
FIG. 5 illustrates an embodiment wherein a main collecting surface is moved in a step-wise manner relative to the sample surface.

FIG. 5 illustrates an embodiment, wherein the different collecting surfaces $\mathbf{24}_1$ for collecting the different cellular bodies do not overlap. This may be achieved by moving the main collecting surface 26 with respect to the sample surface 6 in a step-wise manner as also depicted by the bottom graphs of FIGS. 3A and 3C. To illustrate, collecting surface $\mathbf{24}_1$ may remain provided in holding space 10 for collecting cellular bodies while the sample holder 8 is rotating at a particular value of $\omega^2 r$. After some time, the $\omega^2 r$ value may be incremented at which point in time the sample surface 26 moves with respect to sample surface 6 in order to provide the entire second collecting area $\mathbf{24}_2$ as shown in the holding space so that it can collect a further separated set of one or more cellular bodies.

In such embodiment, the different collecting surfaces may be separated by barriers 30.

Figure 6:
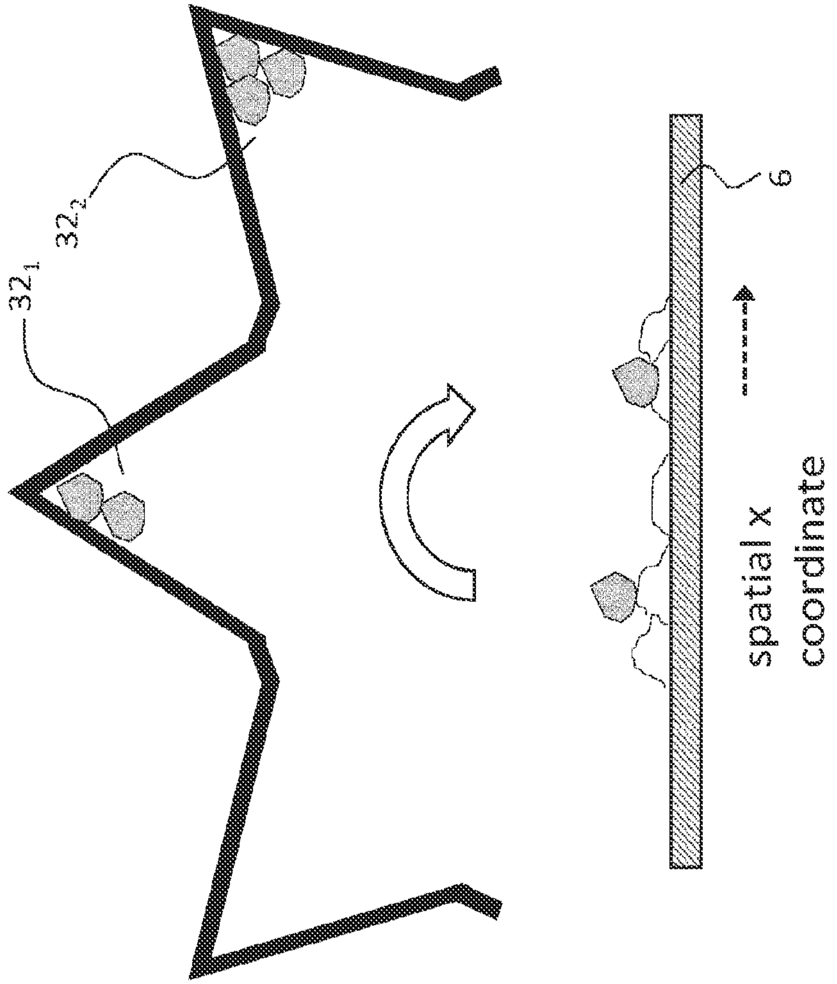
FIG. 6 wherein the collection system comprises a rotating mechanism to provide different reservoirs.

FIG. 6 illustrates an embodiment wherein the step of collecting a separated second set of one or more cellular bodies separately from a first set of one or more cellular bodies comprises collecting the first set of one or more cellular bodies in a first reservoir $\mathbf{32}_1$ and collecting the second set of one or more cellular bodies in a second reservoir $\mathbf{32}_2$ different from the first reservoir.

Preferably, this embodiment also comprises a cellular body focusing system as described herein (not shown in FIG. 6).

In particular, FIG. 6 illustrates an embodiment, wherein the collection system comprises a rotating mechanism to place different collection vials, opposite the sample surface 6 at different time points in order to collect different sets of cellular bodies as described herein.

Of course one could alternatively rotate the whole assembly in the centrifuge in order to change the force direction on the cells, if needed, taking into account the different geometry of the force application.

In the depicted embodiment, it may not be required to use a functionalized collection sample surface since it is likely that if one uses a connical collection vial such as a standard eppendorf tube or centrifuge tube the released cells form a solid pellet in the bottom of the tube which can either be discarded by moving the sample to a different tube or that can be collected if the pellet contains the desired cellular bodies.

Figure 7:
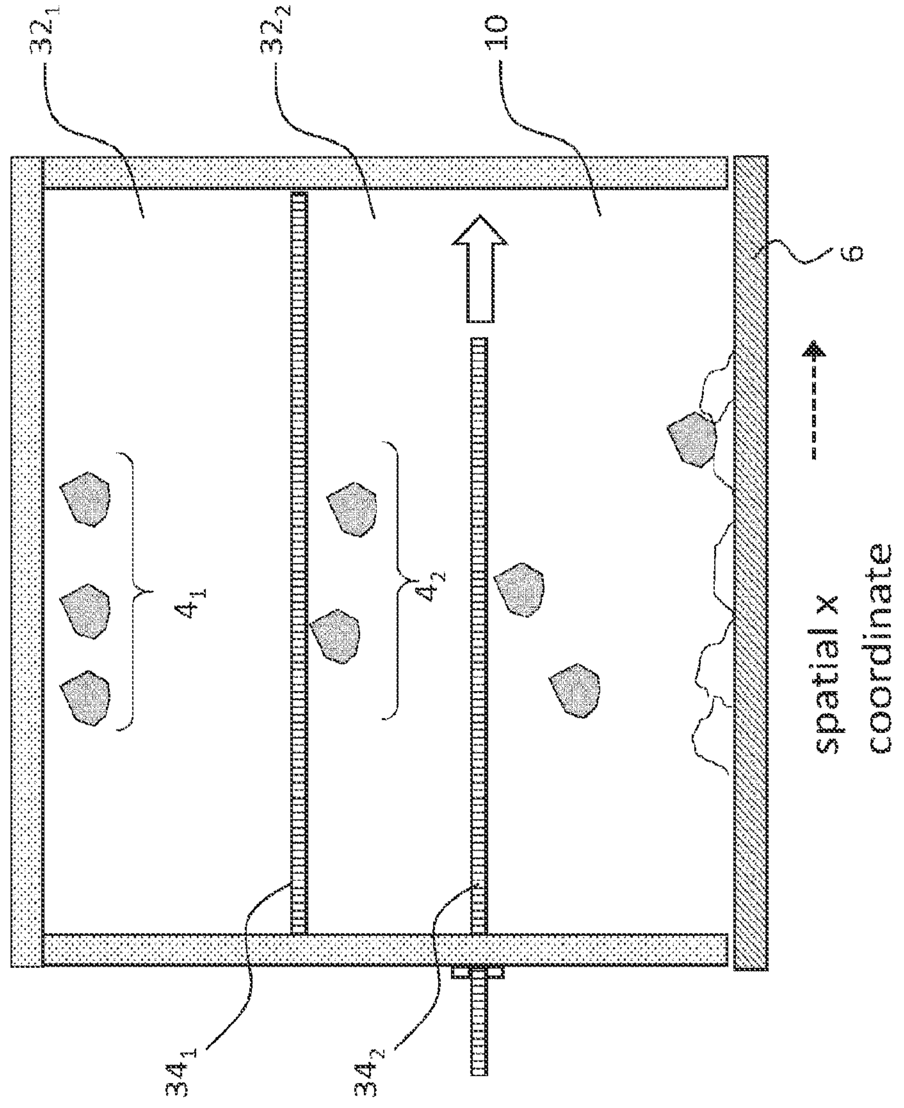
FIG. 7 illustrates an embodiment wherein reservoirs are closed off using barriers.

FIG. 7 schematically depicts an embodiment wherein the collection system is configured to close off a first reservoir $\mathbf{32}_1$ using a first barrier $\mathbf{34}_1$ for collecting a separated first set $\mathbf{4}_1$ of one or more cellular bodies, and to close off a second reservoir $\mathbf{32}_2$ using a second barrier $\mathbf{34}_2$ for collecting a separated second set $\mathbf{4}_2$ of one or more cellular bodies. Herein, the first barrier $\mathbf{34}_1$ may also function as a barrier for keeping the cellular bodies within the second reservoir.

Preferably, this embodiment also comprises a cellular body focusing system as described herein (not shown in FIG. 7).

In particular, FIG. 7 indicates a collection system comprising a collection mechanism using a collection container with mechanical shutters as barriers that can be closed at specific points. First, the system spins at a first value of $\omega_1^2r_1$. Some cellular bodies release and travel to the top of the container. Then a mechanical shutter $\mathbf{34}_1$ closes and defines a compartment with cellular bodies that separated in the $\omega^2r$ range of 0 to $\omega_1^2r_1$. Then the systems spins faster at $w_2^2r_2$ and a second shutter $\mathbf{34}_2$ closes defining a second compartment $\mathbf{32}_2$ containing cellular bodies that separated from the sample surface in the $\omega^2r$ range of $\omega_1^2r_1$ to $w_2^2r_2$. In this way a discrete number of N sets of cellular bodies can be separately collected.

The shutters may be moved using a linear actuator, for example a linear actuator as depicted in FIG. 2C. Further, the shutters may enter into the holding space 10 through an opening that is sealed, e.g. using o-rings or t-rings known in the art, for preventing fluid medium to leak out of the holding space.

Figure 8:
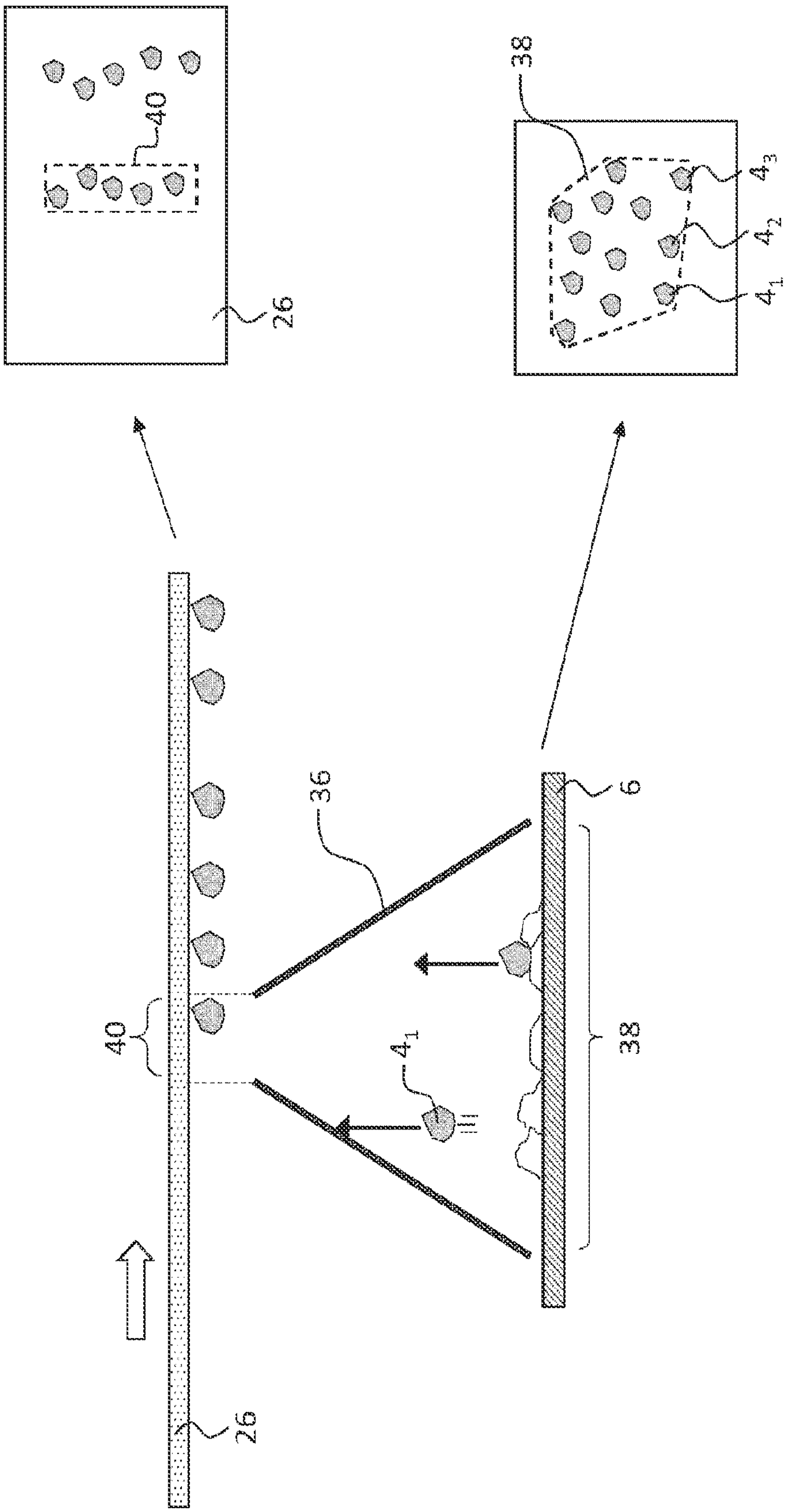
FIG. 8 illustrates an embodiment comprising a cellular body focusing element, in particular a physical cellular body focusing element.

FIG. 8 illustrates an embodiment wherein the system 2 comprises a cellular body focusing system that is configured to focus the separated one or more cellular bodies in the fluid medium after separation from the sample surface. In the depicted embodiment, the cellular body focusing system comprises a physical cellular body focusing element 36, such as a physical funnel 36, for focusing the separated cellular bodies. As shown, the separated one or more cellular bodies 4' travel through the physical cellular body focusing element 36 in the fluid medium.

The right hand side of the figure shows a top view of part of the main collecting surface 26 and a top view of sample surface 6. In the depicted embodiment, it may be understood that the one or more cellular bodies $\mathbf{4}_x$ prior to separation from said sample surface 6 span a particle containing area 38 on said sample surface 6. Due to the cellular body focusing system, the separated one or more cellular bodies 4' are focused in the fluid medium. As a result, they are incident on an area 40 that is smaller than area 38. Hence, the particles that separate at a certain time, or during a certain time period, will occupy a limited area on for example main collecting surface 26. Thus, the focusing may be understood to limit the active area, i.e. the area on main collecting surface 26 that possibly receives separated cellular bodies.

The separated cellular bodies may be focused so that they are incident on a thin line or point. Focusing to a line can be achieved by providing two slanted walls which may force the particles, for example, to exit near the center x-coordinate of the functionalized wall surface. These walls may be coated with a substance that prevents sticking of the particle and reduces friction as the particle moves towards the collection focus. This embodiment prevents spreading of particles that released at a similar force (similar time) over a large area on the main collecting surface.

As said, a funnel can be used above the functionalized wall surface to focus the cellular bodies to a point. In this case the motion of the main collecting surface does not need to be one dimensional but for example by raster scanning or spiral scanning the main collecting surface above the collection point the force can be encoded over a large area of the collection sample surface as indicated in FIG. 4.

Figure 9:
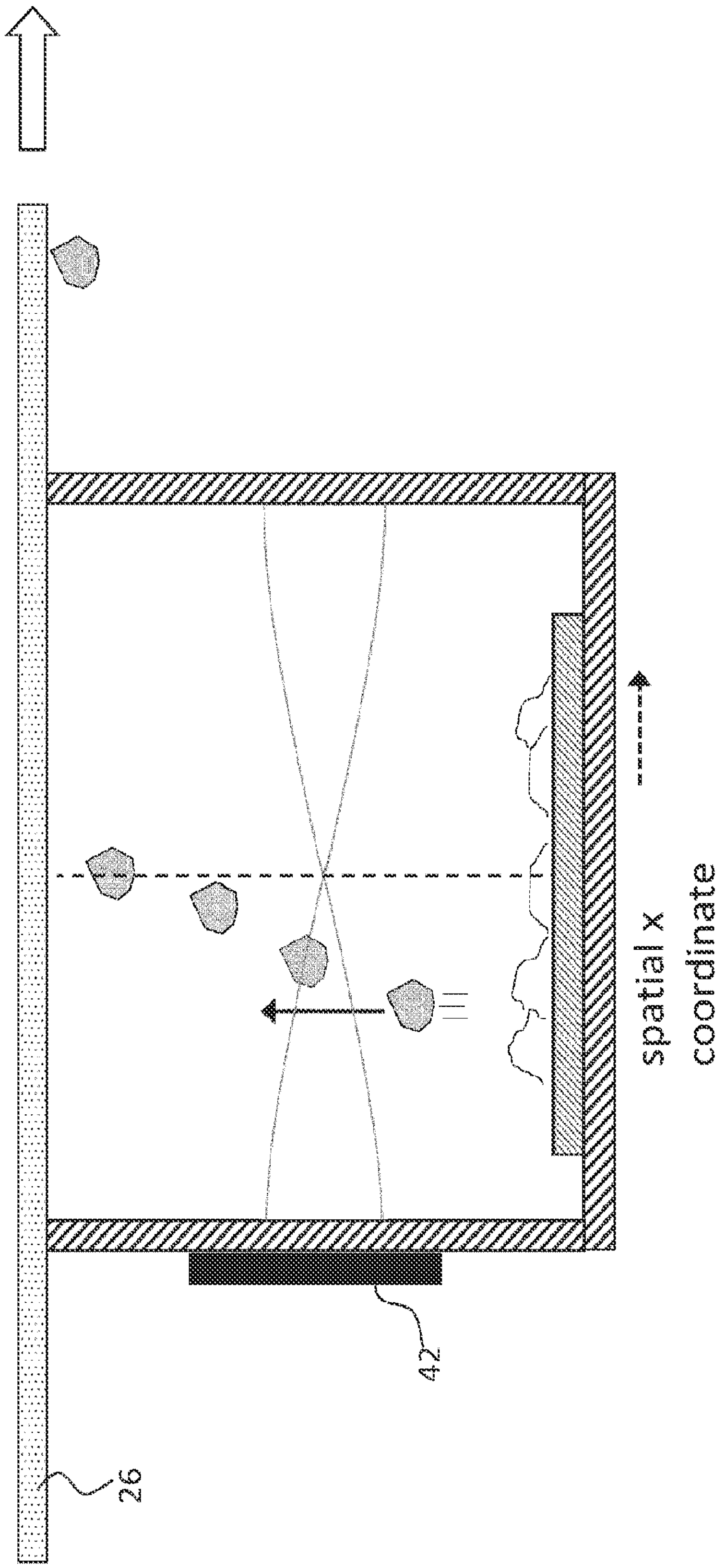
FIG. 9 illustrates an embodiment comprising an acoustic wave generator as cellular body focusing element.

The focusing mechanism does not necessarily need to be a mechanical focusing mechanism: for example focusing may also be achieved by providing an acoustic standing wave in the lateral direction in the fluid medium which forces the cells towards a central node in the chamber. See for example FIG. 9. Alternative embodiments may use for examples electric fields or fluid flow to focus the cells to a central location.

Thus, in an embodiment of the system, the cellular body focusing system comprises an acoustic wave generator 42 that is configured to generated an acoustic wave in the holding space.

Preferably, the acoustic generator is configured to generate an acoustic standing wave in the lateral direction with a node in a central region of the holding space. Separated cellular bodies that are travelling to the collection sample surface 26 will be pushed towards the node of the acoustic field. This is true for cellular bodies with a positive acoustic contrast factor as described previously.

Please note that alternatively any of the focusing embodiments could alternatively also translate the focusing area with respect to the collection surface instead of vice versa.

Figure 10:
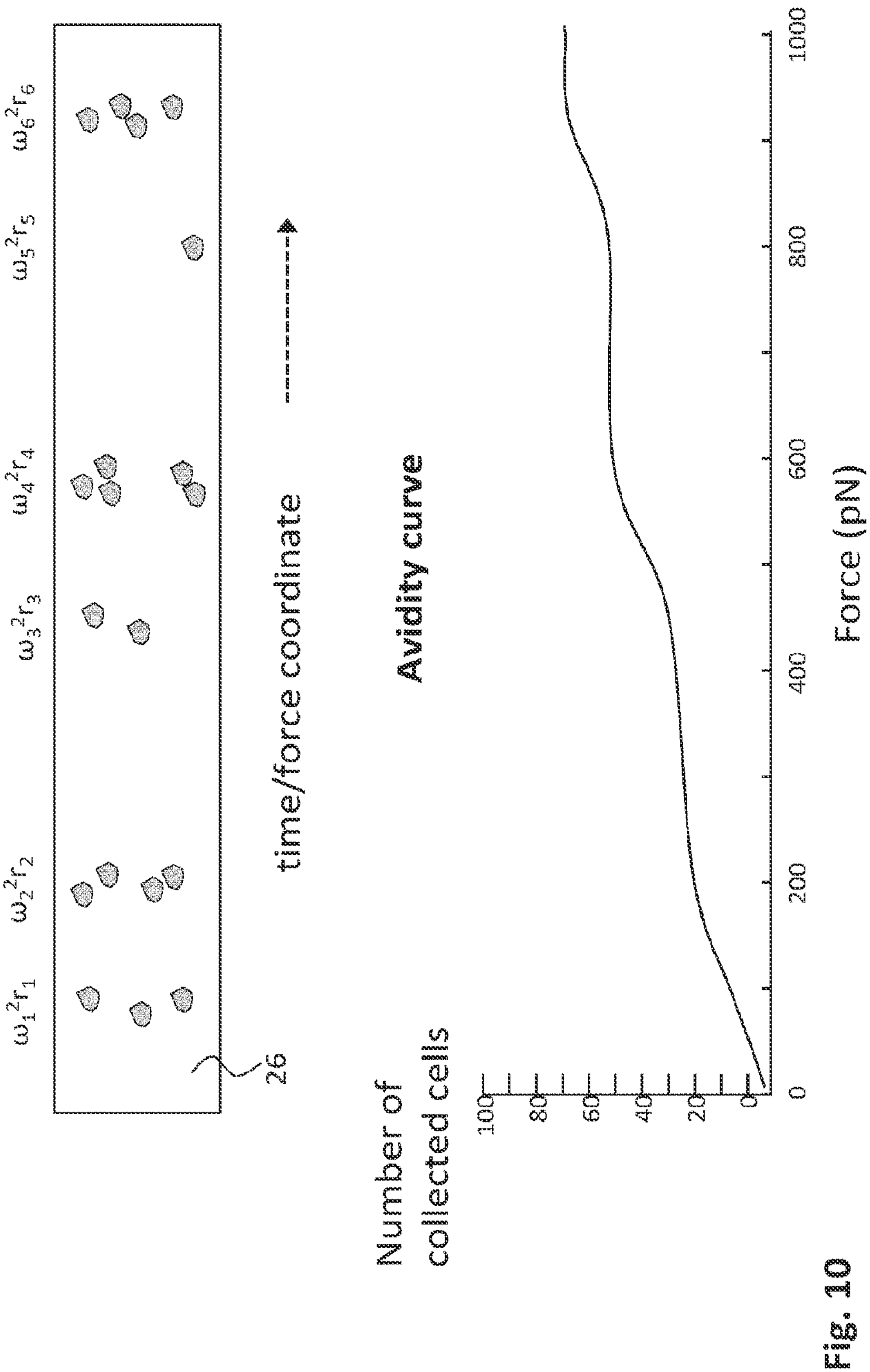
FIG. 10 illustrates how the collected cellular bodies can be analysed to study binding force characteristics.

FIG. 10 shows a main collecting surface 26 which has moved relative to a sample surface. In this example, the system comprised a cellular body focusing element that focused the separated cellular bodies in the fluid medium so that they are incident on a line, or at least a narrow area, on the main collecting surface 26. In this example, the main collecting surface 26 moved relative to the sample surface in a monotonic one dimensional manner in order to encode detachment forces from low to high from left to right on the strip. Multiple cellular bodies can release from different areas of the sample surface for a certain time point corresponding to a detachment force F1, corresponding to a $\omega^2r$ value. The focusing mechanism ensures that these particles form a line on the strip ensuring that cellular bodies that separated at $\omega_1^2r_1$ can be distinguished well from cellular bodies that separated at $w_2^2r_2$ etc. By plotting for example the number of collected cells on the sample surface as a function of $\omega^2r$ one can convert the bands of cellular bodies on the main collecting surface 26 into an avidity curve as shown on the bottom of FIG. 10. Note that the force associated with each $\omega^2r$ value can be determined based on a calibration experiment or on a known volume and density of the cellular bodies and the fluid medium.

Figure 11:
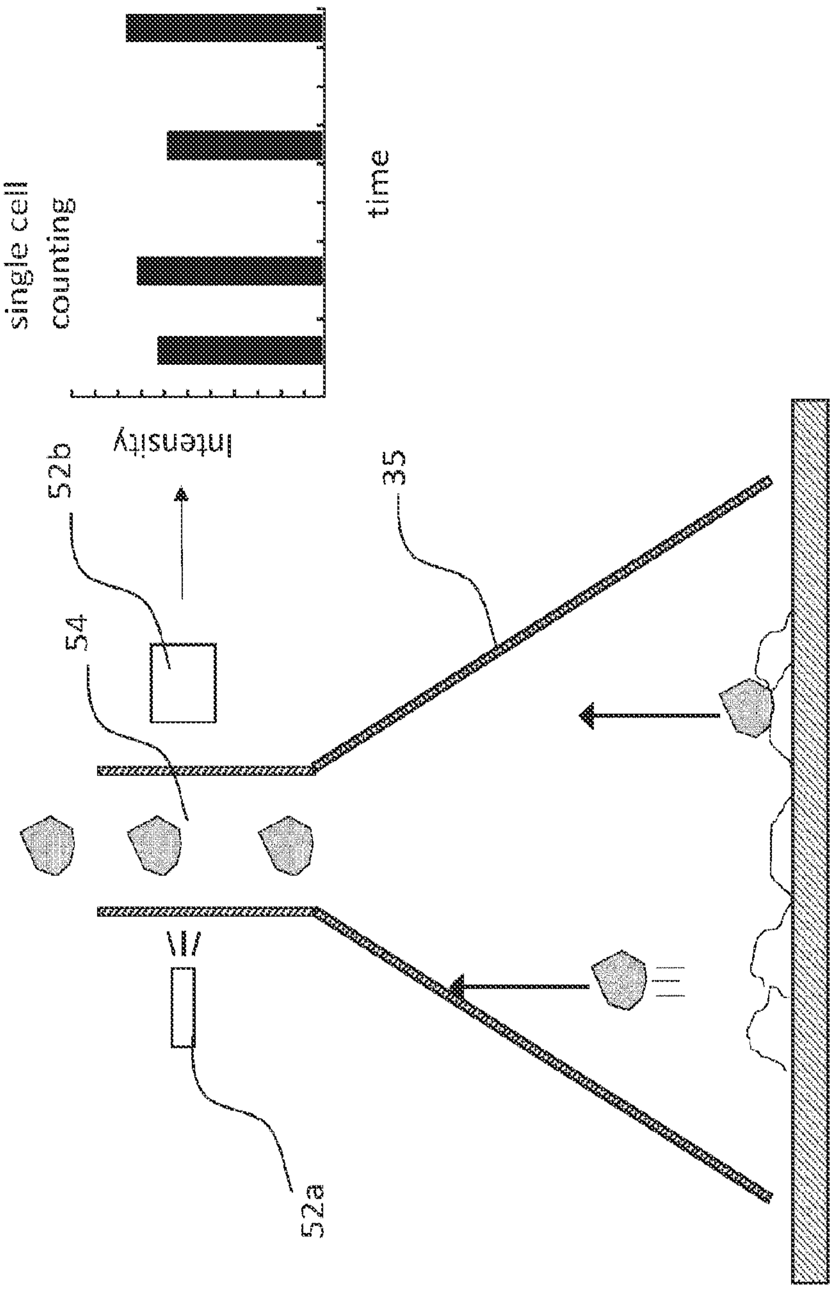
FIG. 11 illustrates an embodiment comprising a detection system for detecting separated cellular bodies.

FIG. 11 illustrates an aspect of this disclosure wherein the system 2 comprises a cellular body focusing system 35 that is configured to focus the separated one or more cellular bodies in the fluid medium alter separation from the sample surface 6. In this aspect, the system 2 further comprises a detection system 52 for detecting the separated one or more cellular bodies in the fluid medium after they have been separated from the sample surface, preferably while the separated one or more cellular bodies are moving through the fluid medium. In the depicted embodiment, the detection system 52 comprises a light source 52*a* and a detector module 52*b* configured to detect light from the light source that is distorted when a cellular body passes through the channel 54. In this aspect, the cellular bodies need not necessarily be collected.

Preferably, the detector monitors the region to which the cellular bodies are focused. When the cellular bodies are sufficiently focused, e.g. into a channel 54, it is possible to count single cellular bodies while the $\omega^2 r$ value is ramped up in order to do online analysis. This detection can be optical, for example based on scattering, absorption, fluorescence or any other optical modality or it may for example be electrical (e.g. based on a change in conductance and/or capacitance in the channel). Fluorescence detection may have the advantage of easy differentiation between different cellular bodies based on standard fluorescent staining techniques known from example from flow cytometry applications. In one embodiment the detector signal may be sent to a data processing system 100 in order for the signal to be processed, for example to provide real time information on the sample. The signal may be sent through a rotating electrical or optical coupler at the rotary joint 22. Please note that, for example in case of using a simple non-imaging optical detector to count pulses as cellular bodies pass by, such a signal is more easily transmitted through a rotary joint (or optionally using wireless transmission) than a camera signal such as described in e.g. US2016/0243560.

Figures 12, 14:
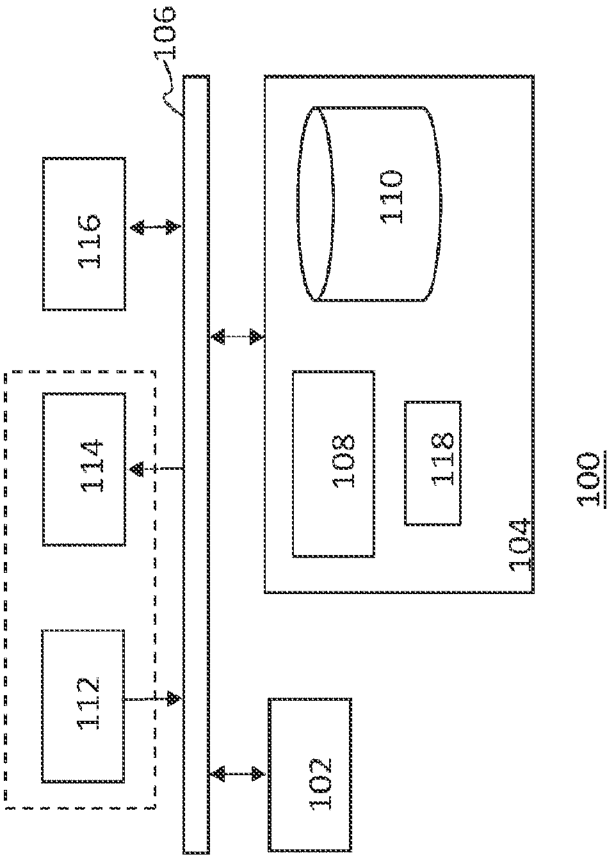
FIG. 12 illustrates data that is stored by a data processing system according to an embodiment.
FIG. 14 illustrates a data processing system according to an embodiment.

FIG. 12 illustrates an example of data that is stored by a data processing system as described herein. In the depicted embodiment, $\omega_1^2 r_1$ is stored in association with the collecting surface 24$_1$, $\omega_2^2 r_1$ is stored in association with the collecting surface 24$_2$, et cetera, in that each collecting surface 24$_x$ is stored in associated with the values $\omega_x$ and $r_x$. Each collecting surface may be indicated by a position or area on a main collecting surface 26 described herein.

The data processing system may also store each value for $\omega_x^2 r_x$ in association with a reservoir 32$_x$, if several reservoirs are used for collecting different sets of one or more cellular bodies.

Figure 13:
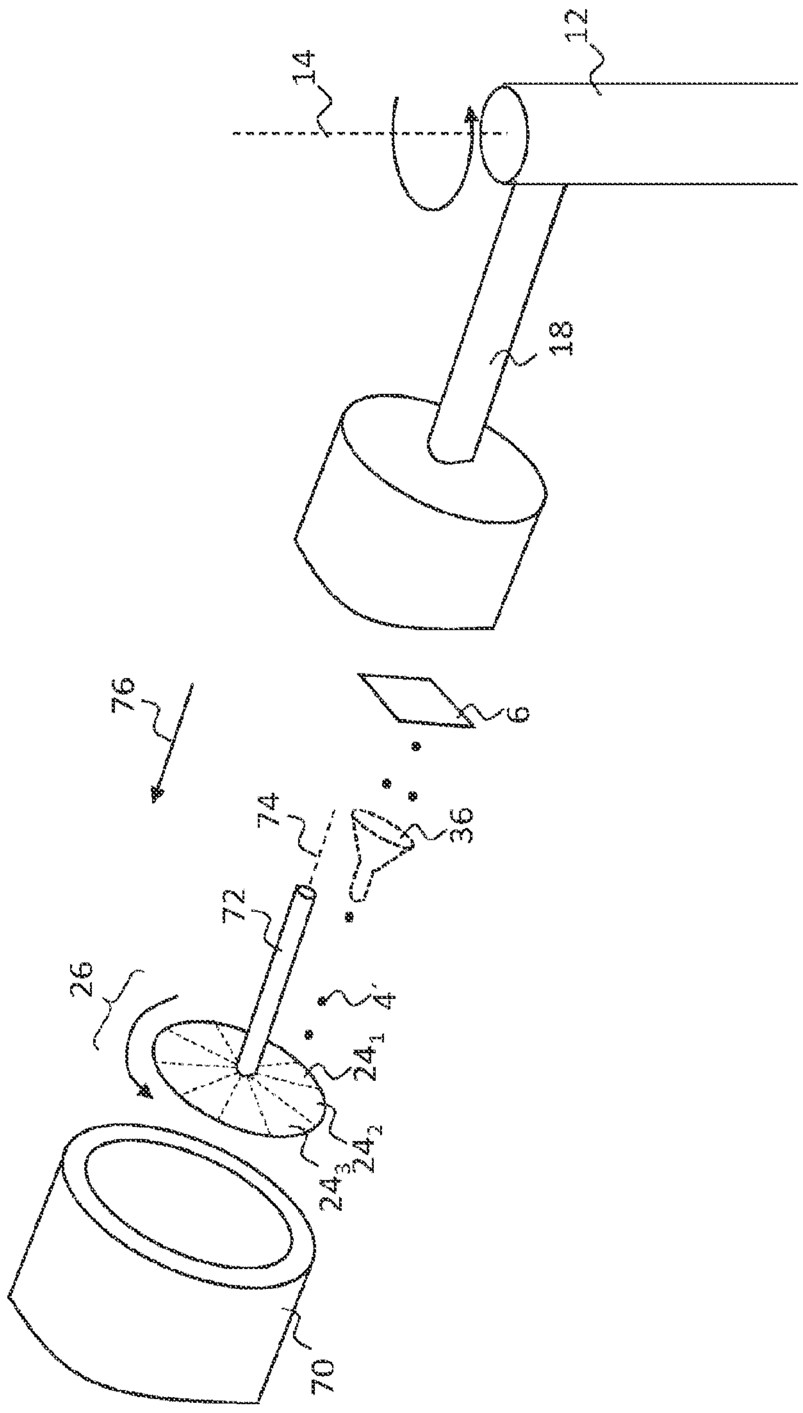
FIG. 13 illustrates an embodiment, wherein a main collecting surface is used for collecting different sets of cellular bodies, wherein the main collecting surface can rotate relative to the sample surface.

FIG. 13 illustrates yet another embodiment, wherein a main collecting surface 26 is used for collecting different sets of cellular bodies, wherein the main collecting surface 26 can rotate relative to the sample surface 6. In the depicted embodiment, the main collecting surface 26 is connected to a rod 72 that can rotate around an axis of rotation indicated by 74. Due to the rotation of rod 72, the main collecting surface 26 also rotates around axis of rotation 74. As a result, different collecting surfaces 24$_x$ are provided as active areas opposite sample surface 6. Arrow 76 indicates the direction of the centrifugal force. Hence, separated cellular bodies 4' are driven towards the area 24$_x$ of main collecting surface 26, which area is positioned opposite sample surface 6. The sample surface 6 is substantially positioned off axis 74.

Rotary arm 18 may be hollow. Rod 72 may, in use, be partially positioned in rotary arm and may be driven by an actuator system that is present in rotary arm 18 as well. If rod 72 is driven by an actuator system outside of the holding space, e.g. by an actuator system in hollow rotary arm 18, then rod 72 passes through a wall of the sample holder. Preferably, a seal, such as an o-ring or t-ring is then used to prevent fluid medium from leaking out of the holding space.

Further shown is a capping seal 70 that is configured to seal the fluid medium, the main collecting surface 26 and sample surface inside holding space 10.

Optionally, this embodiment comprises a cellular body focusing element, such as funnel 36 for focusing the separated cellular bodies in the fluid medium so that they are incident on a relatively small area of main collecting surface 26.

FIG. 14 depicts a block diagram illustrating a data processing system according to an embodiment.

As shown in FIG. 14, the data processing system 100 may include at least one processor 102 coupled to memory elements 104 through a system bus 106. As such, the data processing system may store program code within memory elements 104. Further, the processor 102 may execute the program code accessed from the memory elements 104 via a system bus 106. In one aspect, the data processing system may be implemented as a computer that is suitable for storing and/or executing program code. It should be appreciated, however, that the data processing system 100 may be implemented in the form of any system including a processor and a memory that is capable of performing the functions described within this specification.

The memory elements 104 may include one or more physical memory devices such as, for example, local memory 108 and one or more bulk storage devices 110. The local memory may refer to random access memory or other non-persistent memory device(s) generally used during actual execution of the program code. A bulk storage device may be implemented as a hard drive or other persistent data storage device. The processing system 100 may also include one or more cache memories (not shown) that provide temporary storage of at least some program code in order to reduce the number of times program code must be retrieved from the bulk storage device 110 during execution.

Input/output (U/O) devices depicted as an input device 112 and an output device 114 optionally can be coupled to the data processing system. Examples of input devices may include, but are not limited to, a keyboard, a pointing device such as a mouse, a touch-sensitive display, or the like. Examples of output devices may include, but are not limited to, a monitor or a display, speakers, or the like. Input and/or output devices may be coupled to the data processing system either directly or through intervening I/O controllers.

In an embodiment, the input and the output devices may be implemented as a combined input/output device (illustrated in FIG. 14 with a dashed line surrounding the input device 112 and the output device 114). An example of such a combined device is a touch sensitive display, also sometimes referred to as a "touch screen display" or simply "touch screen". In such an embodiment, input to the device may be provided by a movement of a physical object, such as e.g. a stylus or a finger of a user, on or near the touch screen display.

A network adapter 116 may also be coupled to the data processing system to enable it to become coupled to other systems, computer systems, remote network devices, and/or remote storage devices through intervening private or public networks. The network adapter may comprise a data receiver for receiving data that is transmitted by said systems, devices and/or networks to the data processing system 100, and a data transmitter for transmitting data from the data processing system 100 to said systems, devices and/or networks. Modems, cable modems, and Ethernet cards are examples of different types of network adapter that may be used with the data processing system 100.

As pictured in FIG. 14, the memory elements 104 may store an application 118. In various embodiments, the application 118 may be stored in the local memory 108, the one or more bulk storage devices 110, or apart from the local memory and the bulk storage devices. It should be appreciated that the data processing system 100 may further execute an operating system (not shown in FIG. 14) that can facilitate execution of the application 118. The application 118, being implemented in the form of executable program code, can be executed by the data processing system 100, e.g., by the processor 102. Responsive to executing the application, the data processing system 100 may be configured to perform one or more operations or method steps described herein.

Various embodiments of the invention may be implemented as a program product for use with a computer system, where the program(s) of the program product define functions of the embodiments (including the methods described herein). In one embodiment, the program(s) can be contained on a variety of non-transitory computer-readable storage media, where, as used herein, the expression "non-transitory computer readable storage media" comprises all computer-readable media, with the sole exception being a transitory, propagating signal. In another embodiment, the program(s) can be contained on a variety of transitory computer-readable storage media. Illustrative computer-readable storage media include, but are not limited to: (i) non-writable storage media (e.g., read-only memory devices within a computer such as CD-ROM disks readable by a CD-ROM drive, ROM chips or any type of solid-state non-volatile semiconductor memory) on which information is permanently stored; and (ii) writable storage media (e.g., flash memory, floppy disks within a diskette drive or hard-disk drive or any type of solid-state random-access semiconductor memory) on which alterable information is stored. The computer program may be run on the processor 102 described herein.

The terminology used herein is for the purpose of describing particular embodiments only and is not intended to be limiting of the invention. As used herein, the singular forms "a," "an," and "the" are intended to include the plural forms as well, unless the context clearly indicates otherwise. It will be further understood that the terms "comprises" and/or "comprising." when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of embodiments of the present invention has been presented for purposes of illustration, but is not intended to be exhaustive or limited to the implementations in the form disclosed. Many modifications and variations will be apparent to those of ordinary skill in the art without departing from the scope and spirit of the present invention. The embodiments were chosen and described in order to best explain the principles and some practical applications of the present invention, and to enable others of ordinary skill in the art to understand the present invention for various embodiments with various modifications as are suited to the particular use contemplated.

The invention claimed is:

1. A method for collecting one or more separated cellular bodies in dependence on their binding force with a sample surface that has been prepared with target cells, the method comprising:

providing a sample holder comprising a holding space, wherein the holding space comprises a fluid medium and comprises the sample surface and the one or more cellular bodies in the fluid medium, wherein the one or more cellular bodies are contacting said sample surface with target cells;

rotating the sample holder around an axis of rotation for causing a centrifugal force on the one or more cellular bodies herewith separating the one or more cellular bodies from the sample surface, wherein the rotating comprises:

rotating the sample holder at a first angular velocity, $\omega_1$, the sample surface with target cells being positioned a distance, $r_1$, from an axis of rotation, $\omega_1^2 r_1$ having a first value thus causing a centrifugal force on the one or more cellular bodies herewith separating a first set of one or more cellular bodies from the sample surface with target cells, thus forming a first set of one or more separated cellular bodies; and, rotating the sample holder at a second angular velocity, $\omega_2$, the sample surface with target cells being positioned a distance, $r_2$, from the axis of rotation, $\omega_2^2 r_2$ having a second value higher than said first value, thus causing a centrifugal force on one or more cellular bodies still contacting the sample surface with target cells herewith separating a second set of one or more cellular bodies from the sample surface with target cells, thus forming a second set of one or more separated cellular bodies and, collecting the first and second set of one or more separated cellular bodies after the cellular bodies have been separated from the sample surface with target cells.

2. The method according to claim 1, wherein the collecting comprises:

collecting the first set of one or more separated cellular bodies in the fluid medium after the first set of one or more separated cellular bodies have been separated from the sample surface, and collecting, separately from the first set of one or more separated cellular bodies, the second set of one or more separated cellular bodies in the fluid medium after the second set of one or more separated cellular bodies have been separated from the sample surface.

3. The method according to claim 2, further comprising providing a first collecting surface in the holding space, the first collecting surface being configured to bind the first set of one or more separated cellular bodies, and causing the first set of one or more separated cellular bodies to be incident on the first collecting surface, and providing a second collecting surface in the holding space, the second collecting surface being configured to bind the second set of one or more separated cellular bodies, and causing the second set of one or more separated cellular bodies to be incident on the second collecting surface.

4. The method according to claim 3, wherein providing the first collecting surface and then the second collecting surface comprises moving, a main collecting surface with respect to said sample surface, the main collecting surface comprising the first collecting surface and the second collecting surface.

5. The method according to claim 1, further comprising focusing the one or more separated cellular bodies in the fluid medium after separation from the sample surface.

6. The method according to claim 5, wherein focusing the one or more separated cellular bodies comprises causing the one or more separated cellular bodies to travel through a physical cellular body focusing element in the sample holder.

7. The method according to claim 5, wherein focusing the one or more separated cellular bodies comprises generating an acoustic wave in the holding space.

8. The method according to claim 3, wherein the one or more cellular bodies prior to separation from said sample surface span a particle containing area on said sample surface, the method further comprising focusing the one or more separated cellular bodies in the fluid medium after separation from the sample surface, focusing the first set of one or more separated cellular bodies in the fluid medium so that they are incident on a first area of the first collecting surface, wherein the first area is smaller than the particle containing area on said sample surface, and focusing the second set of one or more separated cellular bodies in the fluid medium so that they are incident on a second area of the second collecting surface, wherein the second area is smaller than the particle containing area on said sample surface.

9. The method according to claim 2, further comprising collecting the first set of one or more separated cellular bodies in a first reservoir and collecting the second set of one or more separated cellular bodies in a second reservoir different from the first reservoir.

10. The method according to claim 9, wherein collecting the first set of one or more separated cellular bodies in a first reservoir comprises closing of the first reservoir using a first barrier, and wherein collecting the second set of one or more separated cellular bodies in the second reservoir comprises closing of the second reservoir using a second barrier, wherein the first barrier functions as a barrier for keeping the cellular bodies within the second reservoir.

11. The method according to claim 2, further comprising collecting the first set of one or more separated cellular bodies in a first reservoir comprising closing of the first reservoir using a first barrier that comprises a barrier collecting surface being configured to bind the second set of one or more separated cellular bodies, and causing the second set of separated cellular bodies to be incident on the barrier collecting surface.

12. The method according to claim 1, comprising removing and collecting the one or more separated cellular bodies from the sample holder, and analyzing the thus obtained one or more separated cellular bodies.

13. A method for detecting one or more separated cellular bodies in dependence on their binding force with a sample surface, the method comprising providing a sample holder comprising a holding space, wherein the holding space comprises a fluid medium and comprises the sample surface and the one or more cellular bodies in the fluid medium, wherein the one or more cellular bodies are contacting said sample surface, and rotating the sample holder around an axis of rotation for causing a centrifugal force on the one or more cellular bodies herewith separating the one or more cellular bodies from the sample surface, wherein the rotating comprises:

rotating the sample holder at a first angular velocity, $\omega_1$, the sample surface with target cells being positioned a distance, $r_1$, from an axis of rotation, $\omega_1^2 r_1$ having a first value thus causing a centrifugal force on the one or more cellular bodies herewith separating a first set of one or more cellular bodies from the sample surface with target cells, thus forming a first set of one or more separated cellular bodies; and, rotating the sample holder at a second angular velocity, $\omega$2, the sample surface with target cells being positioned a distance, $r_2$, from the axis of rotation, $\omega_2^2 r_2$ having a second value higher than said first value, thus causing a centrifugal force on one or more cellular bodies still contacting the sample surface with target cells herewith separating a second set of one or more cellular bodies from the sample surface with target cells, thus forming a second set of one or more separated cellular bodies and, focusing the first and second sets of one or more separated cellular bodies in the fluid medium after separation from the sample surface and detecting the one or more separated cellular bodies in the fluid medium after they have been separated from the sample surface.

* * * * *